US012769063B2

(12) United States Patent
Louh et al.

(10) Patent No.: US 12,769,063 B2
(45) Date of Patent: Oct. 20, 2026

(54) OPTICAL MODULE

(71) Applicant: Advanced Semiconductor Engineering, Inc., Kaohsiung (TW)

(72) Inventors: Shyue-Long Louh, Kaohsiung (TW); Jenchun Chen, Kaohsiung (TW)

(73) Assignee: Advanced Semiconductor Engineering, Inc., Kaohsiung (TW)

( * ) Notice: Subject to any disclaimer, the term of this patent is extended or adjusted under 35 U.S.C. 154(b) by 599 days.

(21) Appl. No.: 18/108,488

(22) Filed: Feb. 10, 2023

(65) Prior Publication Data

US 2024/0272365 A1 Aug. 15, 2024

(51) Int. Cl.

| | |
|---|---|
| ***G02B 6/293*** | (2006.01) |
| ***A61B 5/0205*** | (2006.01) |
| ***A61B 5/024*** | (2006.01) |
| ***G02B 6/42*** | (2006.01) |

(52) U.S. Cl.

CPC ...... *G02B 6/29395* (2013.01); *A61B 5/02427* (2013.01); *G02B 6/4214* (2013.01); *G02B 6/4215* (2013.01); *A61B 5/0205* (2013.01); *A61B 5/02416* (2013.01)

(58) Field of Classification Search

CPC . G02B 6/4215; A61B 5/0205; A61B 5/02416; A61B 5/14552; A61B 5/02427

See application file for complete search history.

(56) References Cited

U.S. PATENT DOCUMENTS

2016/0146639 A1* 5/2016 Chan ........................ G01S 17/04 29/428
2016/0238439 A1* 8/2016 Chu ........................ H10F 77/407
2023/0132704 A1* 5/2023 Tajiri .................... A61B 5/0205 600/324

FOREIGN PATENT DOCUMENTS

CN 217426747 U 9/2022

OTHER PUBLICATIONS

U.S. Appl. No. 17/465,713, filed Sep. 2, 2021, Tang et al.

* cited by examiner

*Primary Examiner* — Tarifur R Chowdhury
*Assistant Examiner* — Paul Schnase
(74) *Attorney, Agent, or Firm* — Foley & Lardner LLP

(57) ABSTRACT

An optical module is disclosed. The optical module includes a carrier, a first optical receiver disposed over the carrier and configured to receive a first light of a first wavelength band, and a second optical receiver disposed over the carrier and configured to receive a second light of a second wavelength band different from the first wavelength band. The optical module also includes a light blocking structure having a first portion around the first optical receiver and the second optical receiver. The light blocking structure is substantially opaque to the first wavelength band and the second wavelength band. The optical module also includes a first optical filter disposed over the first optical receiver and configured to allow the first light to pass through, and a second optical filter disposed over the second optical receiver and configured to allow the second light to pass through.

20 Claims, 19 Drawing Sheets

OPTICAL MODULE

BACKGROUND

1. Field of the Disclosure

The present disclosure relates to an optical module.

2. Description of the Related Art

Electronic wearable devices are becoming increasingly functional and compact. For example, sensors may be integrated into components or packages (such as system in packages (SiPs)) to obtain information or signals reflecting physical activity and/or health through non-invasive optical measurement. However, such measurement may suffer from low signal-to-noise ratio (SNR) since signals obtained are typically weak in comparison to background noise or because of signal attenuation during transmission.

SUMMARY

In some arrangements, an optical module includes a carrier, a first optical receiver disposed over the carrier and configured to receive a first light of a first wavelength band, and a second optical receiver disposed over the carrier and configured to receive a second light of a second wavelength band different from the first wavelength band. The optical module also includes a light blocking structure having a first portion around the first optical receiver and the second optical receiver. The light blocking structure is substantially opaque to the first wavelength band and the second wavelength band. The optical module also includes a first optical filter disposed over the first optical receiver and configured to allow the first light to pass through, and a second optical filter disposed over the second optical receiver and configured to allow the second light to pass through.

In some arrangements, an optical module includes a carrier, a first optical receiver disposed over the carrier and configured to receive a first light from a to-be-inspected object to obtain a first physiological parameter, and a second optical receiver disposed over the carrier and configured to receive a second light from the to-be-inspected object to obtain a second physiological parameter different from the first physiological parameter. The optical module also includes a light blocking structure having a first portion around the first optical receiver and the second optical receiver. The light blocking structure is substantially opaque to the first light and the second light.

In some arrangements, an optical module includes a carrier, a first optical receiver disposed over the carrier and configured to receive a first light of a first wavelength band, and a second optical receiver disposed over the carrier and configured to receive a second light of a second wavelength band different from the first wavelength band. The optical module also includes a first optical filter disposed over the first optical receiver and configured to allow the first light to pass through, and a second optical filter disposed over the second optical receiver and configured to allow the second light to pass through. The optical module also includes a light blocking structure disposed over the carrier. The light blocking structure has a first portion disposed between the first optical receiver and the second optical receiver and configured to block the first light from being received by the second optical receiver.

BRIEF DESCRIPTION OF THE DRAWINGS

Aspects of some arrangements of the present disclosure are readily understood from the following detailed description when read with the accompanying figures. It is noted that various structures may not be drawn to scale, and dimensions of the various structures may be arbitrarily increased or reduced for clarity of discussion.

FIG. 3B-2 is a cross-section of one or more stages of a method of manufacturing an optical module in accordance with some arrangements of the present disclosure.

DETAILED DESCRIPTION

Figure 1A:
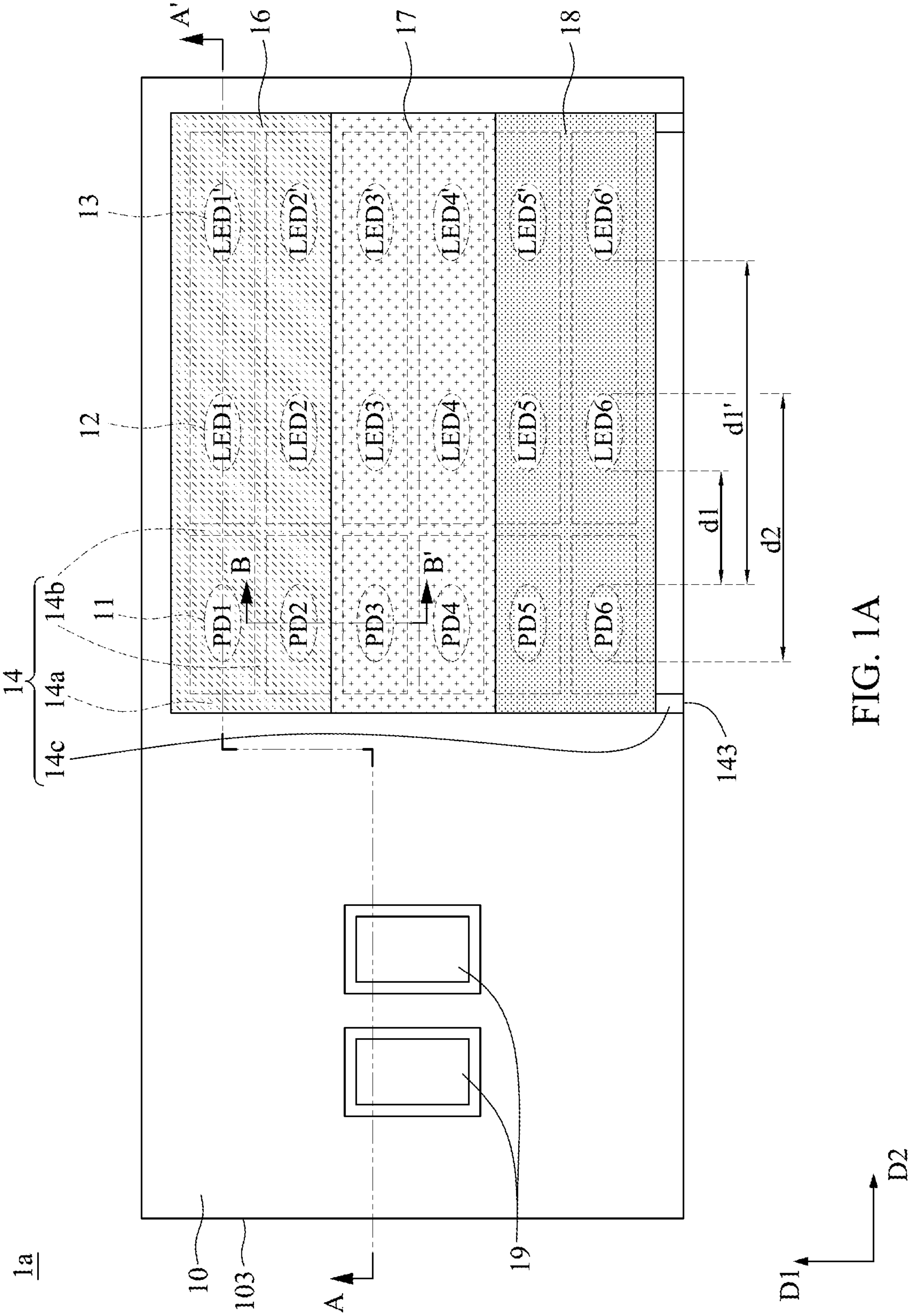
FIG. 1A is a top view of an exemplary optical module according to some arrangements of the present disclosure.

Common reference numerals are used throughout the drawings and the detailed description to indicate the same or similar components. Arrangements of the present disclosure will be readily understood from the following detailed description taken in conjunction with the accompanying drawings.

The following disclosure provides many different arrangements, or examples, for implementing different features of the provided subject matter. Specific examples of components and arrangements are described below to explain certain aspects of the present disclosure. These are, of course, merely examples and are not intended to be limiting. For example, the formation of a first feature over or on a second feature in the description that follows may include arrangements in which the first and second features are formed or disposed in direct contact, and may also include arrangements in which additional features may be formed or disposed between the first and second features, such that the first and second features may not be in direct contact. In addition, the present disclosure may repeat reference numerals and/or letters in the various examples. This repetition is for the purpose of simplicity and clarity and does not in itself dictate a relationship between the various arrangements and/or configurations discussed.

Figure 1B:
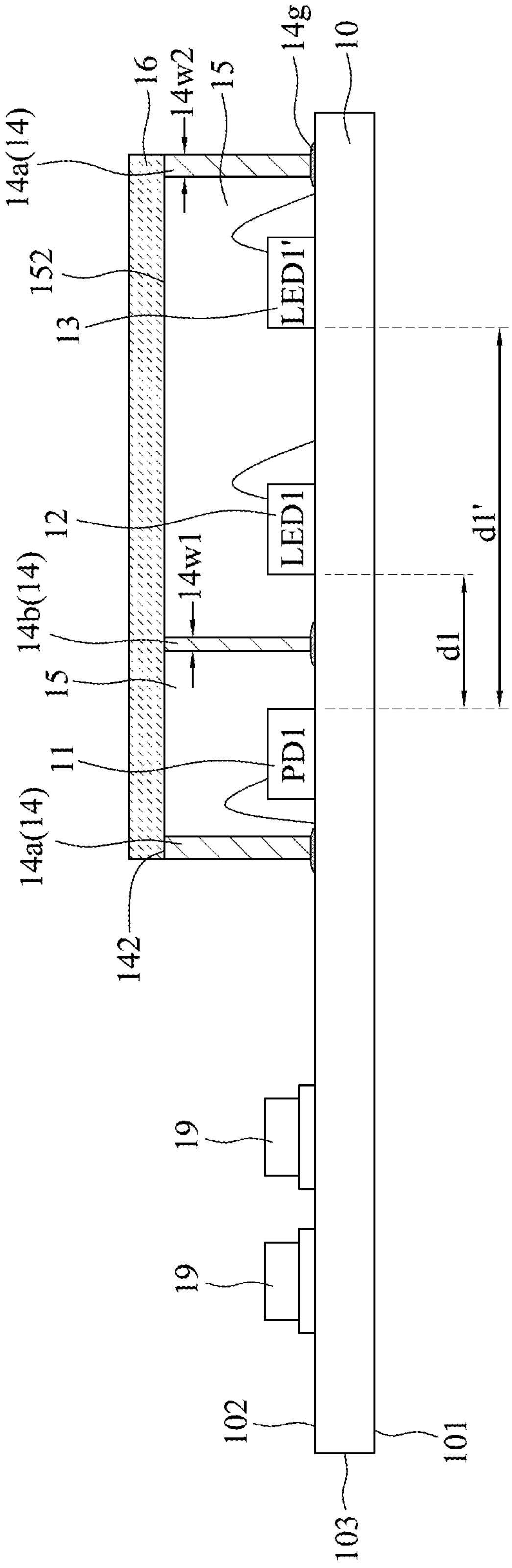
FIG. 1B is a cross-section of an exemplary optical module according to some arrangements of the present disclosure.

FIG. 1A is a top view of an exemplary optical module 1*a* according to some arrangements of the present disclosure. FIG. 1B is a cross-section of an optical module according to some arrangements of the present disclosure. In some arrangements, the cross-section of FIG. 1B is drawn as a cross-section of the optical module 1*a* along line AA'.

The optical module 1*a* may include or be a part of an electronic component or an electronic module, such as a system-in-package (SiP) module. In some arrangements, the optical module 1*a* may include or be a part of a wearable device, such as a smartwatch, a smart band, or another smart wearable device. For example, the optical module 1*a* may be configured to be worn by and/or attached to an object or a target. The object may include a human or an animal. In some arrangements, the optical module 1*a* may include or be a part of a portable electronic device, such as a laptop, a cellular telephone, a tablet, a notebook, a camera, a radio, etc. Configuration or application of the optical module 1*a* in the specification and figures is for illustrative purposes only, and not intended to limit the present disclosure.

The optical module 1*a* may include or be a part of a monitoring device or a detecting device. In some arrangements, the optical module 1*a* may be equipment that detects signals or pieces of information, such as biological signals (or biological parameters), physiological signals (or physiological parameters), motions (e.g., body motions of the human or animal), and/or environmental information in a vicinity of an object or a target. In some arrangements, the optical module 1*a* may include a photoplethysmography (PPG) sensor that can be used to monitor changes in blood volume, pulse rate, oxygen saturation ($SpO_2$), blood pressure, blood vessel stiffness, etc.

In some arrangements, the optical module 1*a* may perform data communication with a base station or a terminal device (such as a mobile phone) in a wireless communications manner, such as via radio frequency identification technology or short-range wireless communications technology. In some arrangements, the optical module 1*a* may be used in combination with a detection device (such as a sensor), an electronic device (such as a signal processing device) and/or other corresponding external devices for further processing acquired signals.

The optical module 1*a* may include a carrier 10, optical receivers PD1, PD2, PD3, PD4, PD5, and PD6 (collectively referred to as optical receivers 11), optical emitters LED1, LED2, LED3, LED4, LED5, and LED6 (collectively referred to as optical emitters 12), optical emitters LED1', LED2', LED3', LED4', LED5', and LED6' (collectively referred to as optical emitters 13), a light blocking structure 14, an encapsulant 15 (illustrated in FIG. 1B), optical elements 16, 17, 18, and an electronic component 19.

The carrier 10 may include a substrate. The carrier 10 may include a printed circuit board (PCB), such as a paper-based copper foil laminate, a composite copper foil laminate, or a polymer-impregnated glass-fiber-based copper foil laminate. The carrier 10 may include a flexible substrate or a flexible printed circuit (FPC). In some arrangements, the carrier 10 may include an interconnection structure, such as a redistribution layer (RDL) or a grounding element.

The carrier 10 may include a surface 101, a surface 102 opposite to the surface 101, and a surface (or a lateral surface) 103 extending between the surface 101 and the surface 102. In some arrangements, the surface 102 may be configured to face an object or a target to be detected or inspected. For example, when the optical module 1*a* is worn by a user, the surface 102 may face the user's skin. In some arrangements, the surface 103 may be the edge or the outermost sidewall.

The carrier 10 may include one or more conductive pads (not shown) in proximity to, adjacent to, or embedded in and exposed by the surface 101 and/or the surface 102. The carrier 10 may include a solder resist (not shown) on the surface 101 and/or the surface 102 to fully expose or expose at least a portion of the conductive pads for electrical connections. In some arrangements, a connector (not shown) may be disposed over or on the surface 101 to provide an electrical connection between the optical module 1*a* and an external component (such as a PCB). In some arrangements, the connector may include one or more solder balls or solder bumps, such as a controlled collapse chip connection (C4) bump, a ball grid array (BGA) or a land grid array (LGA).

Each of the optical receivers 11, each of the optical emitters 12, and each of the optical emitters 13 may be disposed over or on the surface 102 of the carrier 10. Each of the optical receivers 11, each of the optical emitters 12, and each of the optical emitters 13 may be electrically connected to the carrier 10 through solder bonding, Cu-to-Cu bonding, wire bonding, or hybrid bonding.

Each of the optical receivers 11 may be aligned. The optical receivers 11 may be disposed in a column (or disposed along a first direction D1, a vertical direction, or a vertical axis). Each of the optical emitters 12 may be aligned. The optical emitters 12 may be disposed in a column (or disposed along the first direction D1). Each of the optical emitters 13 may be aligned. The optical emitters 13 may be disposed in a column (or disposed along the first direction D1).

The optical receivers 11 may be separated from one another by a portion 14*b* of the light blocking structure 14 that is along the direction D2. The optical emitters 12 may be separated from one another by a portion 14*b* of the light blocking structure 14 that is along the direction D2. Similarly, the optical emitters 13 may be separated from one another by a portion 14*b* of the light blocking structure 14 that is along the direction D2.

One of the optical receivers 11, one of the optical emitters 12, and one of the optical emitters 13 may be aligned. For example, the optical receiver PD1, the optical emitter LED1, and the optical emitter LED1'. The optical receiver PD1, the optical emitter LED1, and the optical emitter LED1' may be disposed in a row (or disposed along a second direction D2 non-parallel to the first direction D1). In some arrangements, the second direction D2 may be a horizontal direction (or a horizontal axis) orthogonal to the first direction D1.

The optical emitters 12 and the optical emitters 13 may be separated from the optical receivers 11 by a portion 14*b* of the light blocking structure 14 that is along the direction D1.

In some arrangements, the optical emitters 12 may be disposed closer to the optical receivers 11 than the optical emitters 13. For example, as shown in FIG. 1B, the distance d1 between the optical receiver PD1 and the optical emitter LED1 may be shorter than the distance d1' between the optical receiver PD1 and the optical emitter LED1'.

The optical receivers 11 may each include a photodetector, a photo-sensor, a photodiode (PD), a charge-coupled device (CCD), a photomultiplier tube, a camera, a spectrometer, or another light-sensitive electronic device. The optical receivers 11 may each be configured to receive light (or EM radiation in the ultraviolet, visible, and/or infrared (IR) spectral regions) and generate electrical signals (e.g., an electrical current). For example, the optical receivers 11 may each convert light energy in the form of photons to an electric current.

The optical receivers 11 may each be configured to receive light from outside of the optical module 1*a*. For example, the optical receivers 11 may each be configured to receive light reflected by an object or a target to be detected or inspected. In some arrangements, the electrical signals from the optical receivers 11 may be further processed (by, for example, an electronic component communicated or collectively used with the optical module 1*a*) to determine a biological parameter of the object or the target.

Each of the optical emitters 12 and each of the optical emitters 13 may include a light emitting diode (LED), a laser diode (such as vertical cavity surface-emitting laser (VCSEL)), a lamp, a laser, any other suitable light source, or a combination thereof. Each of the optical emitters 12 and each of the optical emitters 13 may be configured to generate or emit light (or EM radiation in the ultraviolet, visible, and/or IR spectral regions).

In some arrangements, each of the optical emitters 12 and each of the optical emitters 13 may be configured to emit green light, yellow light, and/or light having a wavelength between about 495 nanometers (nm) and about 595 nm.

In some arrangements, each of the optical emitters 12 and each of the optical emitters 13 may be configured to emit red light and/or light having a wavelength between about 620 nm and about 750 nm.

In some arrangements, each of the optical emitters 12 and each of the optical emitters 13 may be configured to emit IR light and/or light having a wavelength between about 750 nm and about 1 millimeter (mm).

In some arrangements, some of the optical emitters 12 and 13 may be configured to emit light of substantially the same wavelength band. The wavelength band herein refers to a range of wavelengths that may or may not be perceived by human eyes, such as visible red light, visible yellow-green light, or infra-red light. The intensity of the light categorized in a specific wavelength band show a distribution in respect to different wavelengths or frequencies. For example, the optical emitters LED1, LED1', LED2, and LED2' may be configured to emit light of substantially the same wavelength band. For example, the optical emitters LED3, LED3', LED4, and LED4' may be configured to emit light of substantially the same wavelength band. For example, the optical emitters LED5, LED5', LED6, and LED6' may be configured to emit light of substantially the same wavelength band. Light of substantially the same wavelength band may include light of the same color or light of the same wavelength.

In some arrangements, the optical receiver PD1, the optical emitter LED1, and the optical emitter LED1' may be a group of optical components for collaboratively providing an optical measurement function or a light-based sensing function, such as a PPG measurement, for the optical module 1*a*. For example, the optical receiver PD1, the optical emitter LED1, and the optical emitter LED1' may collaboratively function as a PPG sensor. For example, the optical receiver PD1, the optical emitter LED1, and the optical emitter LED1' may collaboratively determine a biological parameter of the object or the target, such as changes in blood volume, pulse rate, oxygen saturation ($SpO_2$), blood pressure, blood vessel stiffness, etc.

Oxygen saturation is a non-invasive measurement of how much hemoglobin is bound to oxygen compared to how much hemoglobin remains unbound. Oxygen saturation is measured by using red light (having a wavelength between about 650 nm and about 660 nm) and IR light (having a wavelength between about 930 nm and about 940 nm). Since oxygenated and deoxygenated hemoglobin differ in absorption of light of different wavelengths, after the light of different wavelengths passes through a human skin tissues such as fingers or toes, light-sensitive sensor can measure the extent of absorption of red and IR wavelengths within those human skin tissues, and estimates the oxygen saturation from the absorption spectrum. For example, oxygen saturation is the fraction of oxygen-saturated hemoglobin relative to total hemoglobin (i.e., summation of unsaturated and saturated hemoglobin) in the blood. Red light and IR light individually experiences different extents of absorption within the human skin tissues, thereby demonstrating different degrees of intensity losses where the discrepancy of the losses can be detected and transformed to electronic signal that transmitted to an amplifying circuit for further computation and output a value indicator.

In some arrangements, the optical receiver PD1, the optical emitter LED1, the optical emitter LED1', the optical receiver PD2, the optical emitter LED2, and the optical emitter LED2' may collaboratively function as a PPG sensor. The number of the optical components of a PPG sensor are for illustrative purposes only, and not intended to limit the present disclosure.

In some arrangements, the light from a PPG sensor may be different from the light from another PPG sensor. For example, the optical emitters LED1, LED1', LED2, and LED2' may be configured to emit green light, yellow light, and/or light having a wavelength between about 495 nm and about 595 nm. The optical emitters LED3, LED3', LED4, and LED4' may be configured to emit red light and/or light having a wavelength between about 620 nm and about 750 nm. The optical emitters LED5, LED5', LED6, and LED6' may be configured to emit IR light and/or light having a wavelength between about 750 nm and about 1 mm.

The shape, position, relative location/position, and number of the optical receivers in FIGS. 1A and 1B are for illustrative purposes only, and not intended to limit the present disclosure. The shape, position, relative location/position, and number of the optical emitters in FIGS. 1A and 1B are for illustrative purposes only, and not intended to limit the present disclosure.

The light blocking structure 14 may be disposed over or on the surface 102 of the carrier 10. The light blocking structure 14 may be fixtured on, connected to, or attached to the carrier 10 through an adhesive layer 14*g*. The adhesive layer 14*g* may include epoxy, resin, or other suitable materials, and may be a paste. The adhesive layer 14*g* may be thermally and/or optically cured.

The light blocking structure 14 may encircle the optical receivers 11, the optical emitters 12, the optical emitters 13, the encapsulant 15, and the optical elements 16, 17, 18. A boundary of the light blocking structure 14 may overlap with a boundary of the optical element 16, a boundary of the optical element 17, and/or a boundary of the optical element 18.

The light blocking structure 14 may include an outermost portion 14*a*. The outermost portion 14*a* may be around the optical receivers 11, the optical emitters 12, and the optical emitters 13. The light blocking structure 14 may include portions (or segments) 14*b* extending along the first direction D1 (or a vertical direction) and arranged along a second direction D2 (or a horizontal direction) distinct from the first direction D1. The light blocking structure 14 may include portions (or segments) 14*b* extending along the second direction D2 and arranged along the first direction D1.

In some arrangements, a length of the portion 14*b* of the light blocking structure 14 along the second direction D2 may be greater than the greatest distance d2 between the optical receiver PD1 and the optical emitter LED1. For example, the portion 14*b* of the light blocking structure 14 along the second direction D2 may exceed the greatest distance d1 between the optical receiver PD1 and the optical emitter LED1. Due to manufacturing variations, distance d1 between an optical receiver and the corresponding optical emitter may be slightly different. The portion 14*b* of the light blocking structure 14 should possess sufficient length to ensure that every optical receiver and the corresponding optical emitter can be covered and thereby preventing optical leakage between adjacent rows of the optical module 1*a*. For example, the portion 14*b* of the light blocking structure 14 along the second direction D2 may extend from the leftmost end of the optical receiver PD1 to the rightmost end of the optical emitter LED1.

In some arrangements, the light blocking structure 14 may include a portion 14*c* connecting to the portion 14*a* and extending till the surface 103 of the carrier 10. The light blocking structure 14 may have a surface 143 substantially coplanar with the surface 103 of the carrier 10.

In some arrangements, the light blocking structure 14 may extend till two opposite edges of the carrier 10. For example, as shown in FIG. 3C, the light blocking structure 14 in the middle row may extends till two opposite edges of the carrier units.

The light blocking structure 14 may define a plurality of spaces or cubicles. The optical receivers 11 may each be disposed in one of the spaces. For example, the optical receiver PD1 may be separated from the other optical components by the light blocking structure 14. For example, the optical receiver PD2 may be separated from the other optical components by the light blocking structure 14.

One of the optical emitters 12 and one of the optical emitters 13 may be disposed in one of the spaces. For example, the optical emitters LED1 and LED1' may be disposed in one of the spaces. For example, the optical emitters LED2 and LED2' may be disposed in one of the spaces.

In some arrangements, the optical emitters LED1, LED2, LED3, LED4, LED5, LED6, LED1', LED2', LED3', LED4', LED5', and LED6' may each be disposed in one of the spaces. For example, the light blocking structure 14 may include a portion or segment for separating the optical emitter LED1 from the optical emitter LED1', for separating the optical emitter LED2 from the optical emitter LED2', for separating the optical emitter LED3 from the optical emitter LED3', etc.

In some arrangements, from the cross-section, the light blocking structure 14 may include a plurality of walls and a width of one of the walls may be substantially constant or unvarying. In some arrangements, from the cross-section, a width 14*w*1 of a wall of the portion 14*b* between the optical receiver PD1 and the optical emitter LED1 may be less than a width 14*w*2 of a wall of the portion 14*a* disposed adjacent to the surface 103 of the carrier 10.

The light blocking structure 14 may be non-transmissive (or substantially opaque) to the light emitted from the optical emitters 12 and the optical emitters 13. In some arrangements, the light blocking structure 14 may be configured to transmit almost no light, and therefore reflect, scatter, or absorb all of it. The light blocking structure 14 may include an opaque material, such as opaque epoxy (e.g., black epoxy), opaque resin, ink, carbon black, photoresist, a metal layer, or other non-transparent materials. In some arrangements, the light blocking structure 14 may include a shielding layer.

The light blocking structure 14 may be configured to avoid crosstalk or leakage between the optical emitters 12 and the optical receivers 11 or different rows and between the optical emitters 13 and the optical receivers 11 or different rows. For example, the light blocking structure 14 may be configured to isolate the optical receivers 11 from the optical emitters 12 and 13 on the same row. For example, the light blocking structure 14 may be configured to prevent the light radiated from the optical emitters 12 and 13 of the same row from being directly received by the optical receivers 11 of the same row. For example, the light blocking structure 14 may be configured to prevent the light radiated from the optical emitters 12 and 13 of the same row from being received by the optical receivers 11 of the same row without being reflected by an object or a target to be detected or inspected.

The light blocking structure 14 may include sections between two adjacent optical emitters arranged along the direction D1. The light blocking structure 14 may be configured to define light transmission paths for the optical emitters 12 and 13. The light blocking structure 14 may prevent interference in the light transmission paths. For example, the light blocking structure 14 may be configured to prevent interference between the optical emitter LED1 and the optical emitter LED2. For example, the light blocking structure 14 may be configured to prevent interference between the optical emitter LED2 and the optical emitter LED3. Therefore, the light blocking structure 14 may help reducing signal interference, and detection can be improved.

The encapsulant 15 (illustrated in FIG. 1B) may be disposed over or on the surface 102 of the carrier 10 to cover or encapsulate the optical receivers 11, the optical emitters 12, and the optical emitters 13. The encapsulant 15 may fill in the plurality of spaces or cubicles defined by the light blocking structure 14. In some arrangements, from the cross-section, the wall of the portion 14*b* of the light blocking structure 14 between the optical receiver PD1 and the optical emitter LED1 may be covered or surrounded by the encapsulant 15.

The encapsulant 15 may include a light transmissive material, such as clear glass, clear plastic, clear gel, clear resin, clear epoxy, sapphire, or other transparent materials. In some arrangements, the encapsulant 15 may be transparent to the light emitted from the optical emitters 12 and 13 of the optical module 1*a*.

The encapsulant 15 may include a surface 152 facing away from the carrier 10. In some arrangements, the surface 152 may be configured to face an object or a target to be detected. For example, when the optical module 1*a* is worn by a user, the surface 152 may face the user's skin. In some arrangements, the surface 152 may be substantially planar or flat. In some arrangements, the surface 152 may be substantially parallel to the surface 102 of the carrier 10. In some arrangements, the surface 152 may be substantially coplanar with a surface 142 (or a top surface) of the light blocking structure 14 facing away from the carrier 10. In some arrangements, the surface 142 of the light blocking structure 14 may be substantially planar.

In some arrangements, the light emitted from the optical emitters 12 and 13 of the optical module 1*a* may be optically coupled to the encapsulant 15. "Optically coupled" is defined herein as including the coupling, attaching, or adhering of two or more regions or layers such that the intensity of light passing from one region to the other is not substantially reduced due to Fresnel interfacial reflection losses due to differences in refractive indices between the regions.

In some arrangements, the light emitted from the optical emitters 12 and 13 of the optical module 1*a* may be directly optically coupled to the encapsulant 15. “Directly optically coupling” a first and second region or material refers to the optical coupling of the regions or materials wherein light travelling through the first region can directly pass into the second region without passing through an intermediate region.

The optical elements 16, 17, and 18 may each be disposed over or on the encapsulant 15. The optical elements 16, 17, and 18 may each directly contact the encapsulant 15. In some arrangements, the interface between the optical element 16 and the encapsulant 15 may be substantially parallel to the surface 102 of the carrier 10.

The optical element 16 may cover the optical receiver PD1, the optical emitter LED1, the optical emitter LED1', the optical receiver PD2, the optical emitter LED2, and the optical emitter LED2'. The optical element 16 may be overlapped with the optical receiver PD1, the optical emitter LED1, the optical emitter LED1', the optical receiver PD2, the optical emitter LED2, and the optical emitter LED2' substantially perpendicular to the surface 102 of the carrier 10.

For example, the optical element 17 may cover the optical receiver PD3, the optical emitter LED3, the optical emitter LED3', the optical receiver PD4, the optical emitter LED4, and the optical emitter LED4'. For example, the optical element 18 may cover the optical receiver PD5, the optical emitter LED5, the optical emitter LED5', the optical receiver PD6, the optical emitter LED6, and the optical emitter LED6'.

In some arrangements, the optical elements 16, 17, and 18 may each include one or more optical coating layers, optical filters, or light filters. In some arrangements, the optical elements 16, 17, and 18 may each include a high refractive material coating layer and a low refractive material coating layer. The high refractive material coating layer and the low refractive material coating layer may be formed to control a reflective index thereof. The high refractive material coating layer may include high refractive inorganic oxides. For example, the high refractive inorganic oxides may include titanium dioxide ($TiO_2$), zirconium dioxide ($ZrO_2$), lithium niobate ($LiNbO_3$), lithium tantalate ($LiTaO_3$), lanthanum titanium ($LaTiO_3$), or the like. The low refractive material coating layer may include low refractive oxides. The low refractive material coating layer may include silicone resin, silica ($SiO_2$), or the like.

In some arrangements, the optical elements 16, 17, and 18 may each be configured to select or filter a spectral band or a spectral component of incoming light.

For example, the optical element 16 may be configured to pass light in a set of wavelengths of interest and filter out other light (or noise). For example, the optical element 16 may be configured to pass green light, yellow light, and/or light having a wavelength between about 495 nm and about 595 nm. For example, the optical element 16 may be configured to pass the light emitted from the optical emitters LED1, LED1', LED2, and LED2'. For example, the optical element 16 may be configured as a band-pass filter to the wavelength band of the light emitted from the optical emitters LED1, LED1', LED2, and LED2'. The wavelength band of the light emitted from the optical emitters LED1, LED1', LED2, and LED2' may be at least partially overlapped with a passing band of the optical element 16. The wavelength band of the light emitted from the optical emitters LED1, LED1', LED2, and LED2' may be broader than a passing band of the optical element 16.

The light emitted from the optical emitters LED1, LED1', LED2, and LED2' may be reflected and received by the optical receivers PD1 and PD2. The optical element 16 may be configured to pass the reflected light and reject (e.g., prevent, block, and/or attenuate) other light (or noise) from reaching the optical receivers PD1 and PD2. In some arrangements, the wavelength band of the light emitted from the optical emitters LED1, LED1', LED2, and LED2' may be broader than or encompass the wavelength band of the light received by the optical receivers PD1 and PD2.

For example, the optical element 17 may be configured to pass red light and/or light having a wavelength between about 620 nm and about 750 nm. For example, the optical element 17 may be configured to pass the light emitted from the optical emitters LED3, LED3', LED4, and LED4'. For example, the optical element 17 may be configured as a band-pass filter to the wavelength band of the light emitted from the optical emitters LED3, LED3', LED4, and LED4'. The wavelength band of the light emitted from the optical emitters LED3, LED3', LED4, and LED4' may be at least partially overlapped with a passing band of the optical element 17. The wavelength band of the light emitted from the optical emitters LED3, LED3', LED4, and LED4' may be broader than a passing band of the optical element 17.

The light emitted from the optical emitters LED3, LED3', LED4, and LED4' may be reflected and received by the optical receivers PD3 and PD4. The optical element 17 may be configured to pass the reflected light and reject (e.g., prevent, block, and/or attenuate) other light (or noise) from reaching the optical receivers PD3 and PD4. In some arrangements, the wavelength band of the light emitted from the optical emitters LED3, LED3', LED4, and LED4' may be broader than or encompass the wavelength band of the light received by the optical receivers PD3 and PD4.

For example, the optical element 18 may be configured to pass IR light and/or light having a wavelength between about 750 nm and about 1 mm. For example, the optical element 18 may be configured to pass the light emitted from the optical emitters LED5, LED5', LED6, and LED6'. For example, the optical element 18 may be configured as a band-pass filter to the wavelength band of the light emitted from the optical emitters LED5, LED5', LED6, and LED6'. The wavelength band of the light emitted from the optical emitters LED5, LED5', LED6, and LED6' may be at least partially overlapped with a passing band of the optical element 18. The wavelength band of the light emitted from the optical emitters LED5, LED5', LED6, and LED6' may be broader than a passing band of the optical element 18.

The light emitted from the optical emitters LED5, LED5', LED6, and LED6' may be reflected and received by the optical receivers PD5 and PD6. The optical element 18 may be configured to pass the reflected light and reject (e.g., prevent, block, and/or attenuate) other light (or noise) from reaching the optical receivers PD5 and PD6. In some arrangements, the wavelength band of the light emitted from the optical emitters LED5, LED5', LED6, and LED6' may be broader than or encompass the wavelength band of the light received by the optical receivers PD5 and PD6.

In some arrangements, the carrier 10 may be at least partially transparent to environmental light (e.g., light outside of the wave band of light emitted from the optical emitters 11 and 12). The optical elements 16, 17, and 18 may cover the optical emitters 11 and 12. For example, the optical element 16 covering the optical emitters LED1, LED1', LED2, and LED2' may filter the environmental light and prevent the environmental light from being received by the optical receivers 11.

In some arrangements, the passing band of the optical element 16, the passing band of the optical element 17, and the passing band of the optical element 18 may be non-overlapped with one another. For example, as shown in FIG. 1J, FIG. 1J is a graph of relative intensity of light L2 and Light L3 as a function of wavelength according to some arrangements of the present disclosure. Two curves of FIG. 1J represent the lights L2 and L3 emitted by the optical emitters LED2 and LED3. The relative intensity indicates the relative radiant energy per unit time. The passing band 16*p* of the optical element 16 is superimposed on FIG. 1J to show the optical property of the materials that optical element 16 is composed of. The passing band 16*p* of the optical element 16 allows a portion of light L2 with an even narrower wavelength band to pass, in some embodiments, the passing band 16*p* encompasses the wavelength of light L2 at and around its peak of intensity. The passing band 17*p* of the optical element 17 is superimposed on FIG. 1J to show the optical property of the materials that optical element 17 is composed of. The passing band 17*p* of the optical element 17 allows a portion of light L3 with an even narrower wavelength band to pass, in some embodiments, the passing band 17*p* encompasses the wavelength of light L3 at and around its peak of intensity.

The electronic component 19 may be disposed over or on the surface 102 of the carrier 10 and aside to the optical receivers 11, the optical emitters 12, the optical emitters 13, the light blocking structure 14, the encapsulant 15, and the optical elements 16, 17, 18. The electronic component 19 may be electrically connected to the carrier 10 through solder bonding, Cu-to-Cu bonding, wire bonding, or hybrid bonding.

In some embodiments, the electronic component 19 may include a processor, a controller, a memory, or an input/output (I/O) buffer, etc. In some embodiments, the electronic component 19 may include, for example, a central processing unit (CPU), a microprocessor unit (MPU), a graphics processing unit (GPU), a microcontroller unit (MCU), an application-specific integrated circuit (ASIC), a field-programmable gate array (FPGA), or other types of integrated circuits (ICs). In some embodiments, the electronic component 19 may include an analog front end circuits and/or a driver circuit.

In some arrangements, the electronic component 19 may be configured to control the optical emitters 12 and the optical emitters 13. For example, the electronic component 19 may be configured to provide brightness control and/or color control of the optical emitters 12 and the optical emitters 13.

In some arrangements, the electronic component 19 may be configured to control the optical emitters 12 and the optical emitters 13 based on the one or more properties of the light received by the optical receivers 11. For example, the electronic component 19 may be configured to analyze one or more characteristics of electrical signals from the optical receivers 11. The electrical signals may be related to one or more properties of the light, such as luminous flux (or luminous power or brightness), luminous intensity, propagation direction, wavelength (or frequency, or bandwidth), polarization state, etc.

The positions and number of the electronic components in the optical module 1*a* are not intended to limit the present disclosure. For example, there may be any number of electronic components in the optical module 1*a* due to design requirements.

Figure 1C:
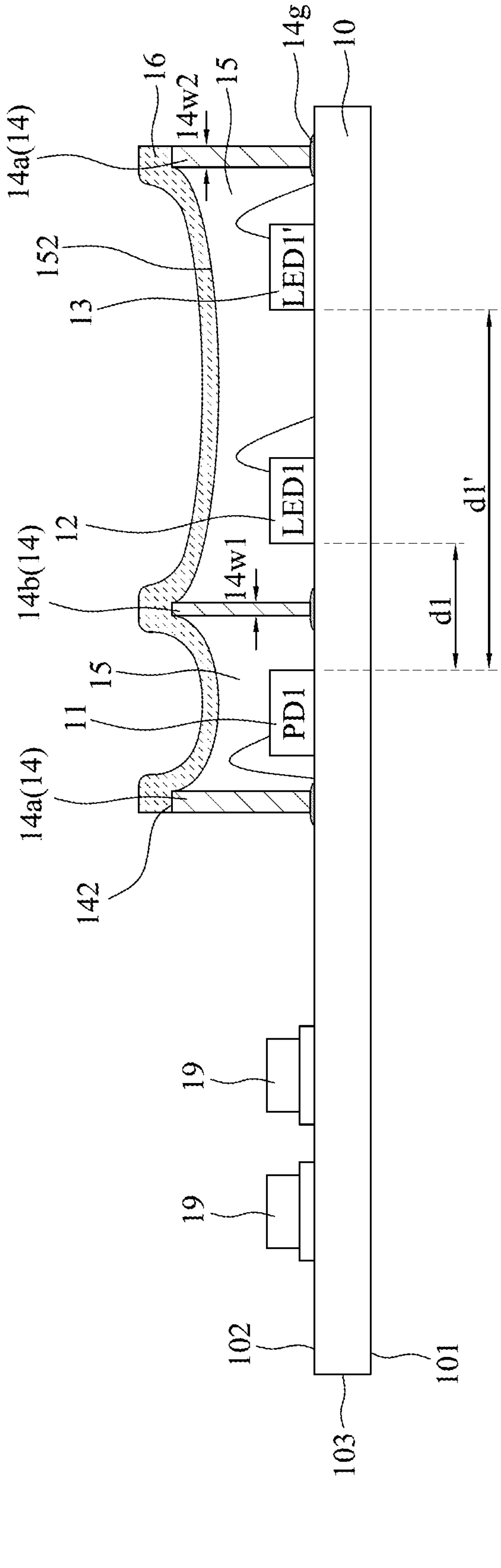
FIG. 1C is a cross-section of an exemplary optical module according to some arrangements of the present disclosure.
Figure 1E:
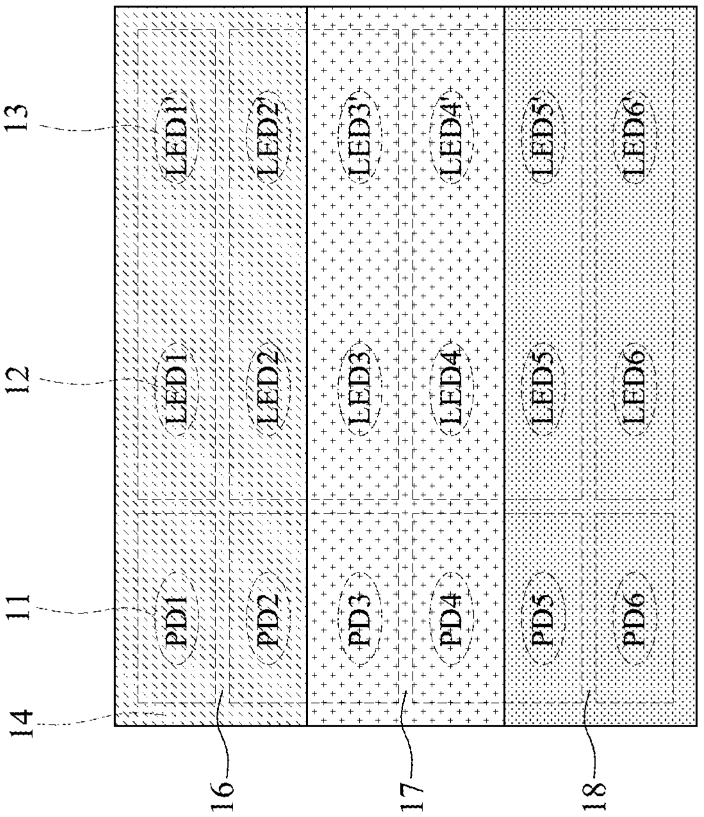
FIG. 1E is a top view of an exemplary part of an optical module according to some arrangements of the present disclosure.

FIG. 1C is a cross-section of an exemplary optical module according to some arrangements of the present disclosure. In some arrangements, the cross-section of FIG. 1C is drawn as a cross-section of the optical module 1*a* along line AA'. The cross-section of FIG. 1C is similar to the cross-section of FIG. 1B with differences therebetween as follow.

The surface 152 of the encapsulant 15 may be curved. For example, the surface 152 may be recessed inwardly. In some arrangements, the surface 152 may be recessed inwardly in one or more of the spaces or cubicles defined by the light blocking structure 14. For example, the surface 152 may be recessed toward the optical receiver PD1. For example, the surface 152 may be recessed toward the optical emitters LED1 and LED1'. In some arrangements, an elevation of the surface 152 may be lower than the surface 142 (or a top surface) of the light blocking structure 14 facing away from the carrier 10. In some arrangements, the bottom (or the lowest point, the lowest elevation) of the surface 152 may be lower than the surface 142 (or a top surface) of the light blocking structure 14 facing away from the carrier 10.

In some arrangements, the optical element 16 may be disposed along the curvature of the surface 152 of the encapsulant 15. For example, the interface between the optical element 16 and the encapsulant 15 may be curved.

In some arrangements, the optical element 16 may form a convex lens (or a concave-convex lens) over the encapsulant 15. In some arrangements, the optical element 16 may form convex lenses (or concave-convex lenses) over one or more of the spaces or cubicles defined by the light blocking structure 14.

The shape of the optical element 16 and the encapsulant 15 may be adjusted according to design requirements and are not intended to limit the present disclosure. For example, in the light transmission paths, the optical element 16 and the encapsulant 15 may construct a panel, a waveguide, a prism, a concave lens, a convex lens, a flat surface, a diffuser, a shutter, a filter, a holographic element, etc.

Figure 1D:
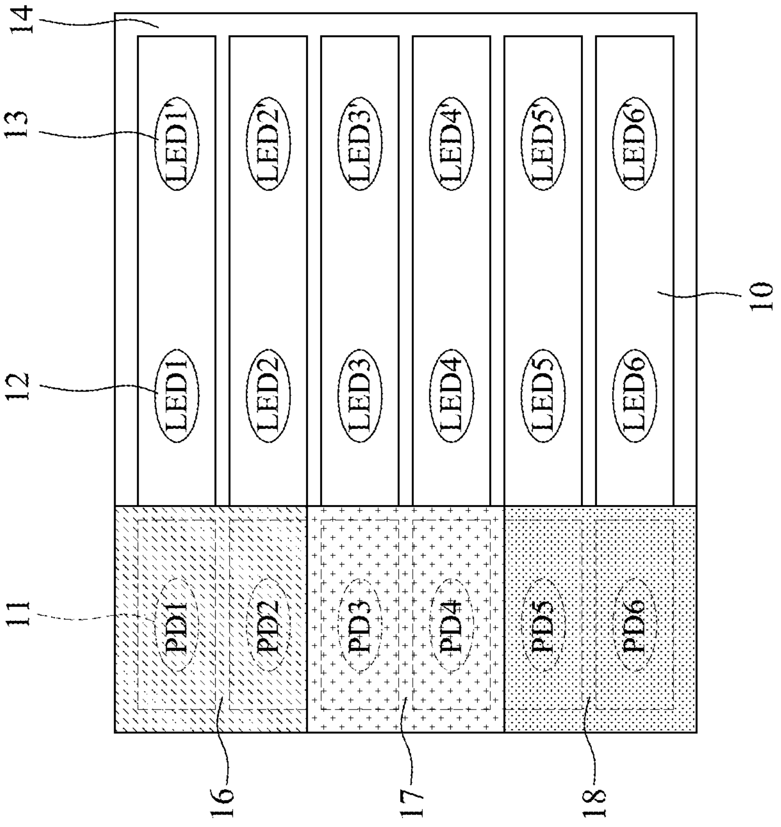
FIG. 1D is a top view of an exemplary part of an optical module according to some arrangements of the present disclosure.

FIG. 1D is a top view of an exemplary part of an optical module according to some arrangements of the present disclosure. The part of the optical module in FIG. 1D is similar to a part of the optical module 1*a* in FIG. 1A with differences therebetween as follow.

The optical element 16 may not cover the optical emitters LED1, LED1', LED2, and LED2'. The optical element 16 may be non-overlapped with the optical emitters LED1, LED1', LED2, and LED2' substantially perpendicular to the surface 102 of the carrier 10.

The optical element 17 may not cover the optical emitters LED3, LED3', LED4, and LED4'. The optical element 18 may not cover the optical emitters LED5, LED5', LED6, and LED6'. The optical element 16 may filter the environmental light or the light from the optical emitters LED1, LED1', LED2, and LED2'. The optical element 17 may filter the environmental light or the light from the optical emitters LED3, LED3', LED4, and LED4'. The optical element 18 may filter the environmental light or the light from the optical emitters LED5, LED5', LED6, and LED6'.

The number and the locations of the optical elements may be adjusted according to design requirements and are not intended to limit the present disclosure. By not covering the optical emitters, the manufacturing cost may be reduced.

FIG. 1E is a top view of an exemplary part of an optical module according to some arrangements of the present disclosure. The part of the optical module in FIG. 1E is similar to a part of the optical module 1*a* in FIG. 1A with differences therebetween as follow.

A PPG sensor may not be separated from another PPG sensor by the light blocking structure 14. For example, the optical receivers PD1 and PD2 may not be separated from the optical receivers PD3 and PD4 by the light blocking structure 14. For example, the optical emitters LED1, LED1', LED2, and LED2' may not be separated from the optical emitters LED3, LED3', LED4, and LED4' by the light blocking structure 14.

Figure 1F:
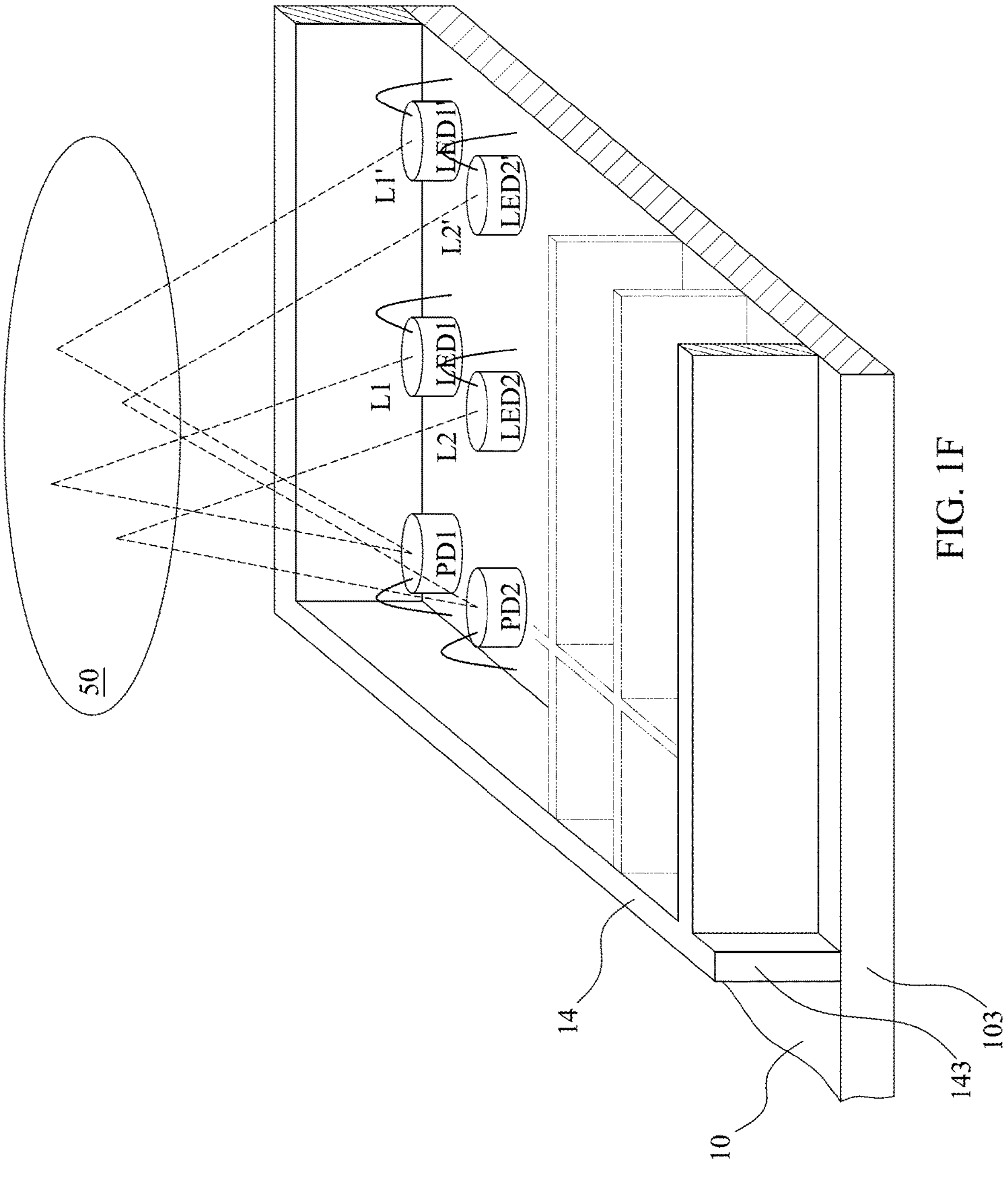
FIG. 1F is a perspective view of an exemplary part of an optical module according to some arrangements of the present disclosure.

FIG. 1F is a perspective view of an exemplary part of an optical module according to some arrangements of the present disclosure. In some arrangements, the perspective view of FIG. 1F is drawn as a perspective view of a part of the optical module 1*a* in FIG. 1A.

The optical emitter LED1 may emit a light L1 and the optical emitter LED1' may emit a light L1'. The light L1 and L1' from the optical emitters LED1 and LED1' is emitting toward an object to be inspected or a target to be inspected 50. The object to be inspected or a target to be inspected 50 may scatter or reflect at least a portion of the light L1 and L1' and the scattered or reflected light may return toward the optical module and be received by the optical receiver PD1.

The optical emitter LED2 may emit a light L2 and the optical emitter LED2' may emit a light L2'. The light L2 and L2' from the optical emitters LED2 and LED2' may be received by (or may radiate) an object or a target. The object or the target may scatter or reflect at least a portion of the light L2 and L2' and the scattered or reflected light may return toward the optical module and be received by the optical receiver PD2.

In some arrangements, the optical receiver PD1, the optical emitter LED1, the optical emitter LED1', the optical receiver PD2, the optical emitter LED2, and the optical emitter LED2' may collaboratively function as a PPG sensor.

In some arrangements, the optical receiver PD1, the optical receiver PD2, and/or an electronic component communicated or collectively used with the optical module may be configured to calculate an absorption coefficient and/or a scattering coefficient of the light L1, L1', L2, and L2' based on spatially resolved diffuse reflectance spectroscopy (SRDRS). For example, an absorption coefficient and/or a scattering coefficient may be calculated using the distance between the optical emitter and the optical receiver, the luminous intensity of the light, and/or the time of flight of the light. The absorption coefficient and/or a scattering coefficient of the light L1, L1', L2, and L2' may be related to one or more properties of the light, such as luminous flux (or luminous power or brightness), luminous intensity, propagation direction, wavelength, polarization state, etc.

In some arrangements, the optical emitters LED1, LED1', LED2, and LED2' may be configured to emit light during different time intervals. For example, the optical emitter LED1 may emit the light L1 during a first time interval and the optical emitter LED1' may emit the light L1' during a second time interval. The optical emitter LED2 may emit the light L2 during a third time interval and the optical emitter LED2' may emit the light L2' during a fourth time interval.

In some arrangements, some of the optical emitters LED1, LED1', LED2, and LED2' may be configured to emit light during the same time interval. For example, during a first time interval, the optical emitter LED1 may emit the light L1 and the optical emitter LED2 may emit the light L2. For example, during a second time interval, the optical emitter LED1' may emit the light L1' and the optical emitter LED2' may emit the light L2'.

In some arrangements, some of the optical emitters LED1, LED1', LED2, and LED2' may be configured to emit light simultaneously. For example, the optical emitter LED1 and the optical emitter LED2 may emit light simultaneously. For example, the optical emitter LED1' and the optical emitter LED2' may emit light simultaneously.

In some comparative arrangements, a light-based sensing measurement may suffer from low signal-to-noise ratio (SNR) since signals obtained are typically weak in comparison to background noise or because of signal attenuation during transmission.

According to some arrangements of the present disclosure, by using the light blocking structure 14 to define the light transmission paths and using the optical elements 16, 17, and 18 to filter out noise, the SNR can be increased, the problem of transmission loss can be solved, and detection can be improved.

Figure 1G:
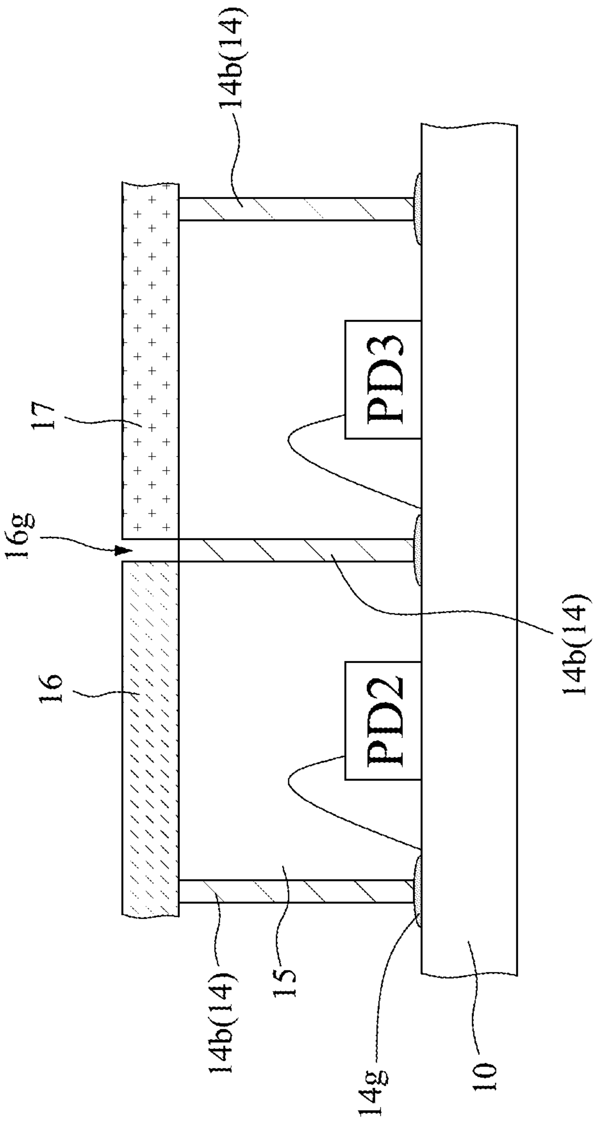
FIG. 1G is a cross-section of an exemplary optical module according to some arrangements of the present disclosure.

FIG. 1G is a cross-section of an exemplary optical module according to some arrangements of the present disclosure. In some arrangements, the cross-section of FIG. 1G is drawn as a cross-section of the optical module 1*a* along line BB'.

In some arrangements, the optical element 16 may be spaced apart from the optical element 17 by a gap 16*g*. For example, the optical element 16 may not contact the optical element 17. In some arrangements, the gap 16*g* may exist over the portion 14*b* of the light blocking structure 14.

Figure 1H:
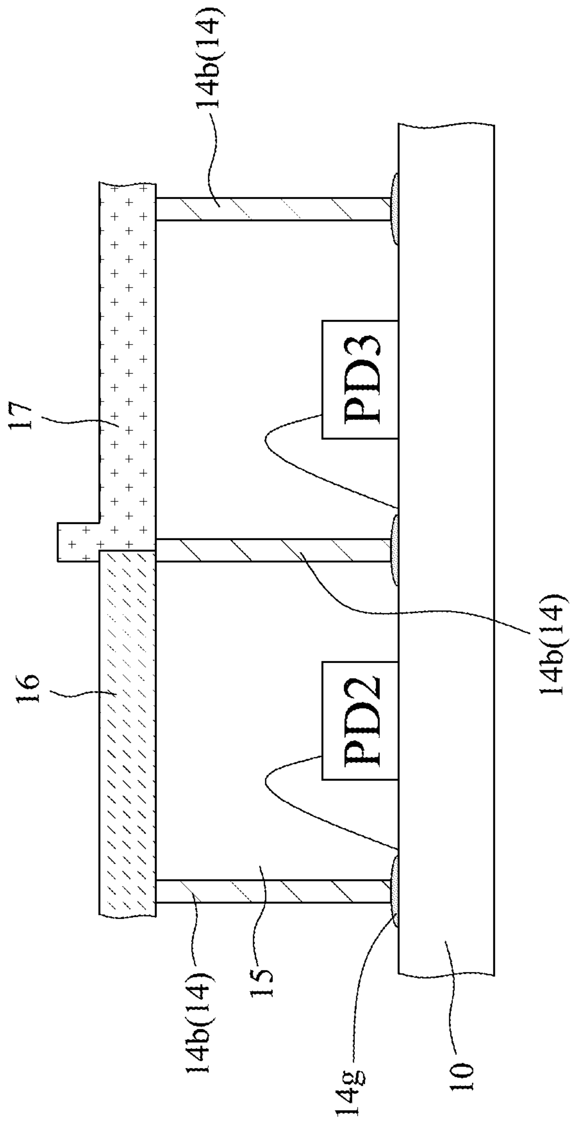
FIG. 1H is a cross-section of an exemplary optical module according to some arrangements of the present disclosure.

FIG. 1H is a cross-section of an exemplary optical module according to some arrangements of the present disclosure. In some arrangements, the cross-section of FIG. 1H is drawn as a cross-section of the optical module 1*a* along line BB'.

In some arrangements, the optical element 16 and the optical element 17 may be partially overlapped over the portion 14*b* of the light blocking structure 14. In some arrangements, the optical element 16 and the optical element 17 may be partially overlapped on the portion 14*b* of the light blocking structure 14. In some arrangements, the optical element 17 may cover the optical element 16. In some other arrangements, the optical element 16 may cover the optical element 17, depending on the formation sequence of the optical element, for example. In some arrangements, a projection area of the optical element 16 on the carrier 10 and a projection area of the optical element 17 on the carrier 10 may be partially overlapped. In some arrangements, the overlapped projection area of the optical element 16 and the optical element 17 may be located between the optical receivers PD2 and PD3.

Figure 1I:
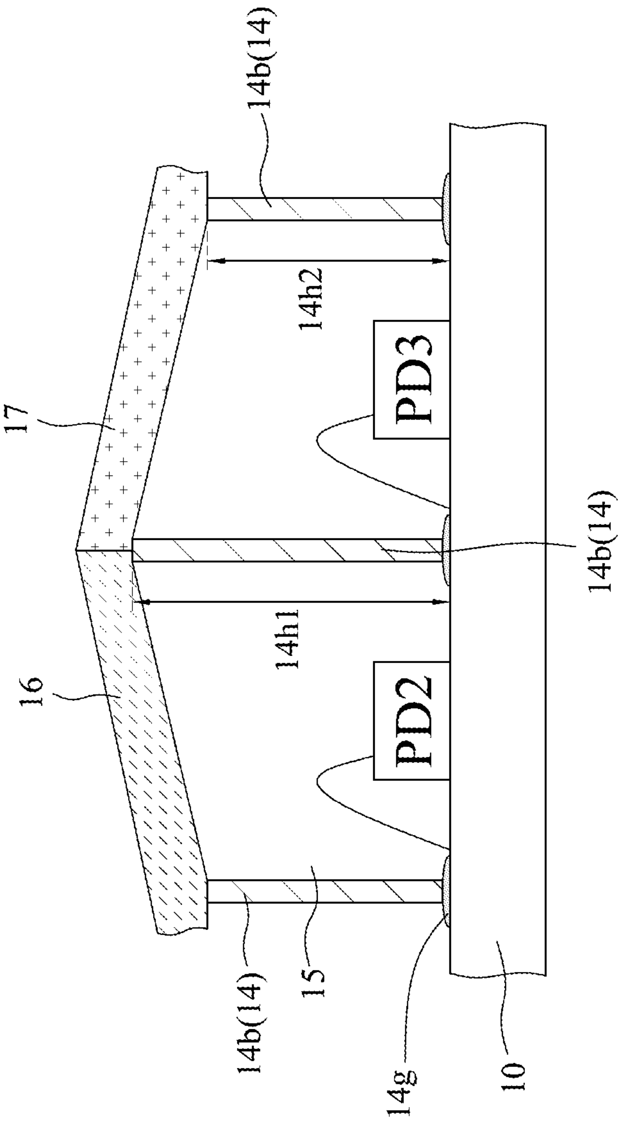
FIG. 1I is a cross-section of an exemplary optical module according to some arrangements of the present disclosure.
Figure 1J:
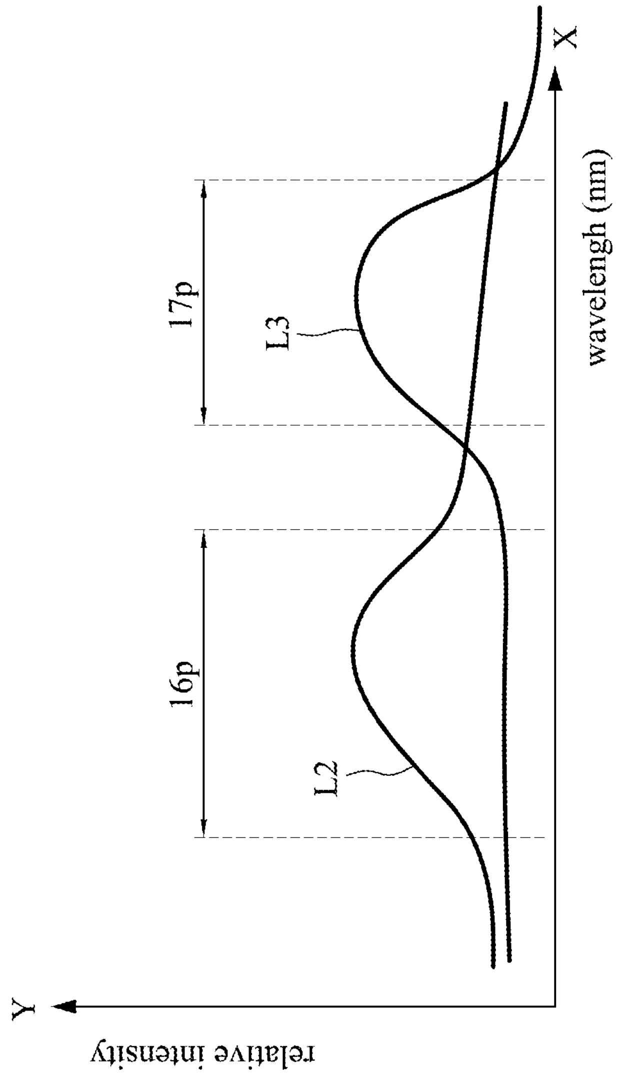
FIG. 1J is a graph of relative intensity of light as a function of wavelength according to some arrangements of the present disclosure.

FIG. 1I is a cross-section of an exemplary optical module according to some arrangements of the present disclosure. In some arrangements, the cross-section of FIG. 1I is drawn as a cross-section of the optical module 1*a* along line BB'.

In some arrangements, the height 14*h*1 of the portion 14*b* of the light blocking structure 14 between the optical receivers PD2 and PD3 may be different from the height 14*h*2 of the portion 14*b* of the light blocking structure 14 not between the optical receivers PD2 and PD3. In some arrangements, the height 14*h*1 of the portion 14*b* of the light blocking structure 14 between the optical receivers PD2 and PD3 may be greater than the height 14*h*2 of the portion 14*b* of the light blocking structure 14 not between the optical receivers PD2 and PD3. In some arrangements, the height of the portion 14*b* of the light blocking structure 14 may be greater than the height of the outermost portion 14*a* (in FIG. 1A) of the light blocking structure 14.

Figure 1K:
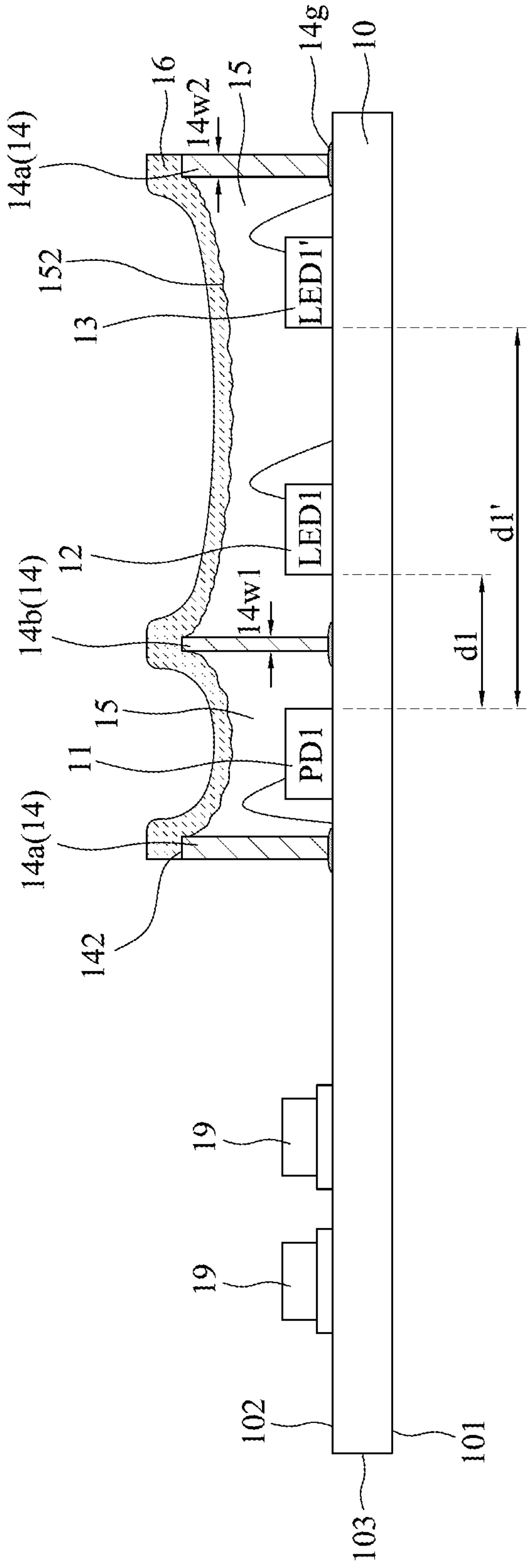
FIG. 1K is a cross-section of an exemplary optical module according to some arrangements of the present disclosure.

FIG. 1K is a cross-section of an exemplary optical module according to some arrangements of the present disclosure. In some arrangements, the cross-section of FIG. 1K is drawn as a cross-section of the optical module 1*a* along line AA' The cross-section of FIG. 1K is similar to the cross-section of FIG. 1B with differences therebetween as follow.

The surface 152 of the encapsulant 15 may be substantially non-planar or non-even. In some arrangements, the interface between the optical element 16 and the encapsulant 15 may be non-planar or non-even.

Figure 2A:
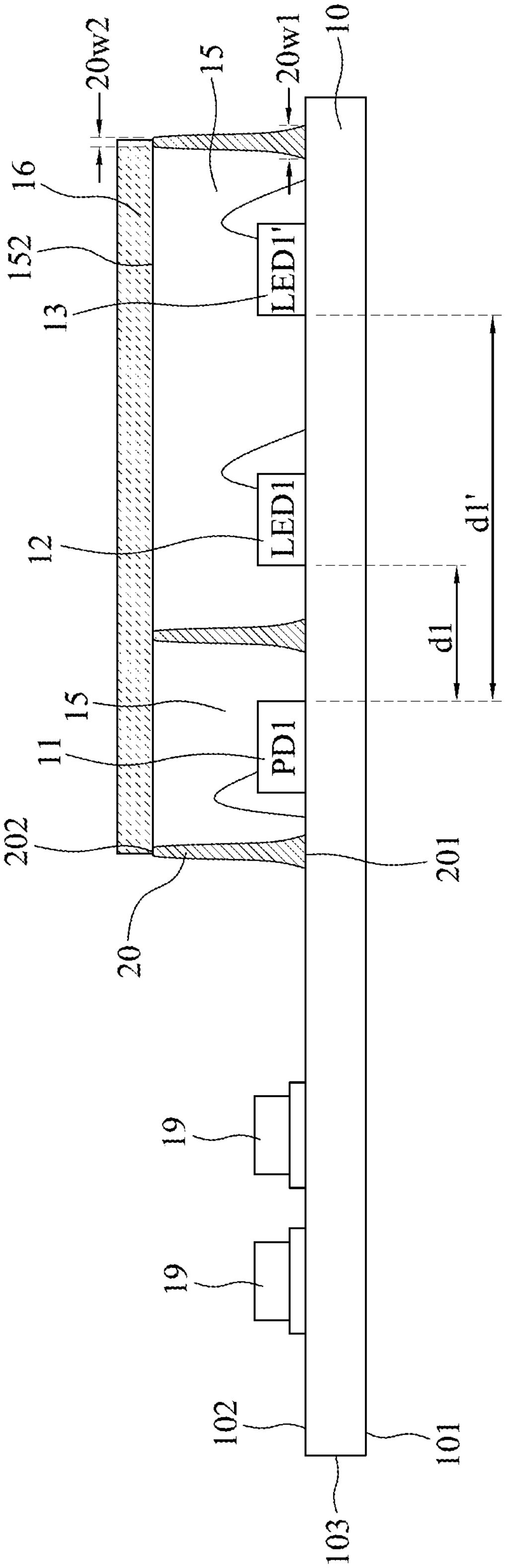
FIG. 2A is a cross-section of an exemplary optical module according to some arrangements of the present disclosure.

FIG. 2A is a cross-section of an exemplary optical module according to some arrangements of the present disclosure. The cross-section of FIG. 2A is similar to the cross-section of FIG. 1B with differences therebetween as follow.

The light blocking structure 20 may be similar to the light blocking structure 14. Therefore, some details of the light blocking structure 20 may correspond to the paragraphs described, and a description thereof is not repeated hereinafter for conciseness.

The light blocking structure 20 may directly contact the carrier 10. The light blocking structure 20 may have a side or an end 201 closer to the carrier 10 and an opposite side or end 202 farther from the carrier 10. A width 20*w*1 of the end 201 may be greater than a width 20*w*2 of the end 202. The light blocking structure 20 may taper from the end 201 to the end 202. The light blocking structure 20 may taper away from the carrier 10. The light blocking structure 20 may include a tapered width away from the carrier 10 from a cross-sectional view. In some arrangements, a cross-sectional area of the light blocking structure 20 proximal to the carrier 10 may be greater than a cross-sectional area of the light blocking structure 20 distal from the carrier 10. In some arrangements, the surface (or top surface) of the light blocking structure 20 facing away from the carrier 10 may be substantially non-planar.

Figure 2B:
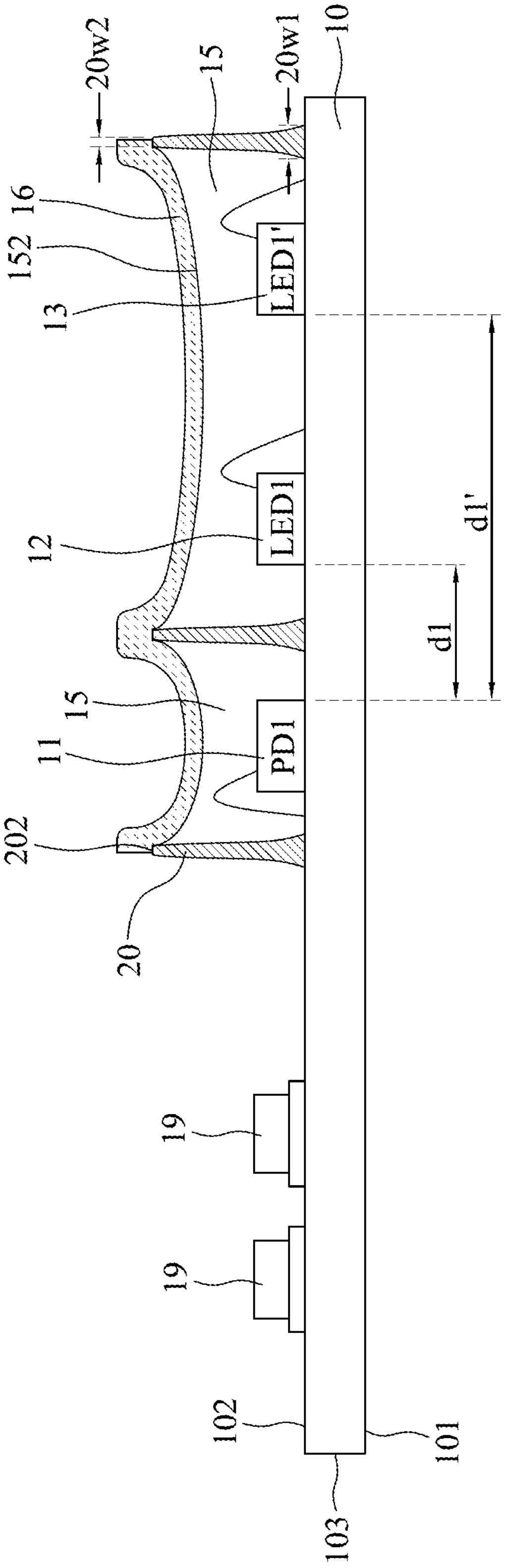
FIG. 2B is a cross-section of an exemplary optical module according to some arrangements of the present disclosure.

FIG. 2B is a cross-section of an exemplary optical module according to some arrangements of the present disclosure. The cross-section of FIG. 2B is similar to the cross-section of FIG. 2A except that the surface 152 of the encapsulant 15 is curved. Some details of the surface 152 of the encapsulant 15 may correspond to the paragraphs described above with respect to FIG. 1C, and a description thereof is not repeated hereinafter for conciseness.

FIGS. 3A, 3B-1, 3C, 3D, 3E, and 3F are top views of one or more stages of a method of manufacturing an optical module in accordance with some arrangements of the present disclosure.

At least some of these figures have been simplified to better illustrate the aspects of the present disclosure. In some arrangements, the optical module 1*a* may be manufactured through the operations described with respect to FIGS. 3A, 3B-1, 3C, 3D, 3E, and 3F.

Figure 3A:
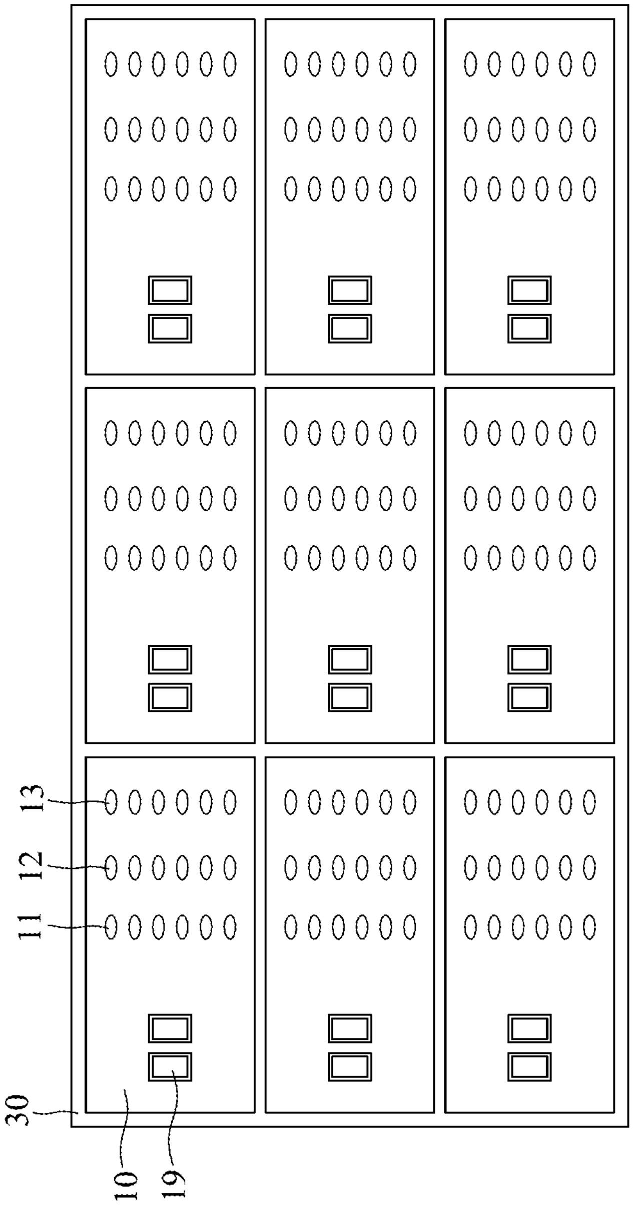
FIGS. 3A, 3B-1, 3C, 3D, 3E, and 3F are top views of one or more stages of a method of manufacturing an optical module in accordance with some arrangements of the present disclosure.

Referring to FIG. 3A, a temporary carrier 30 is provided. In some arrangements, the temporary carrier 30 may include several carrier units, wherein one may be separable from another by a scribe line (not shown). Each of the carrier units is subjected to similar or identical processes in the manufacturing method. Each of the carrier units may include a carrier 10. The optical receivers 11, the optical emitters 12, the optical emitters 13, and the electronic component 19 are disposed over or on the carrier 10.

Figures 1, 3B:
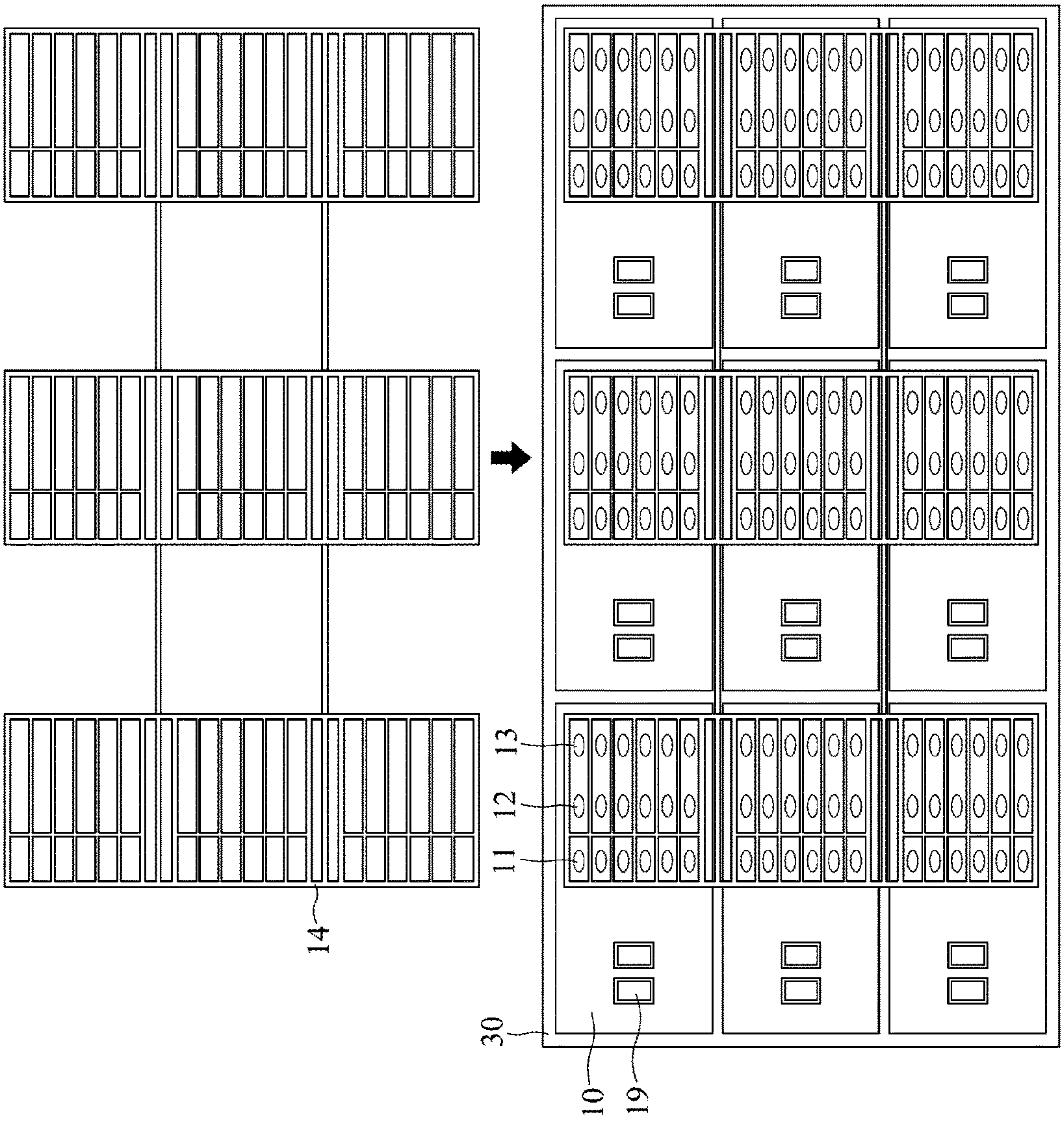

Referring to FIG. 3B-1, the light blocking structure 14 is formed over or on the carrier 10 to define a plurality of spaces or cubicles. In some arrangements, a plurality of the light blocking structures 14 may be formed by an injection molding operation and then be attached to the temporary carrier 30. The plurality of the light blocking structures 14 may be connected to one another. The plurality of the light blocking structures 14 may each be connected or attached to one of the carriers 10 through an adhesive layer (such as the adhesive layer 14*g* in FIG. 1B). In some arrangements, the adhesive layer may be thermally and/or optically cured.

In some arrangements, the plurality of the light blocking structures 14 may be formed individually. For example, the plurality of the light blocking structures 14 may be formed by a three-dimensional (3D) printing operation and/or a dispensing operation. In some arrangements, from the cross-section (e.g., FIG. 1B), the light blocking structure 14 formed by an injection molding operation or a 3D printing operation may include a plurality of walls and a width of one of the walls may be substantially constant or unvarying.

Figures 2, 3B:
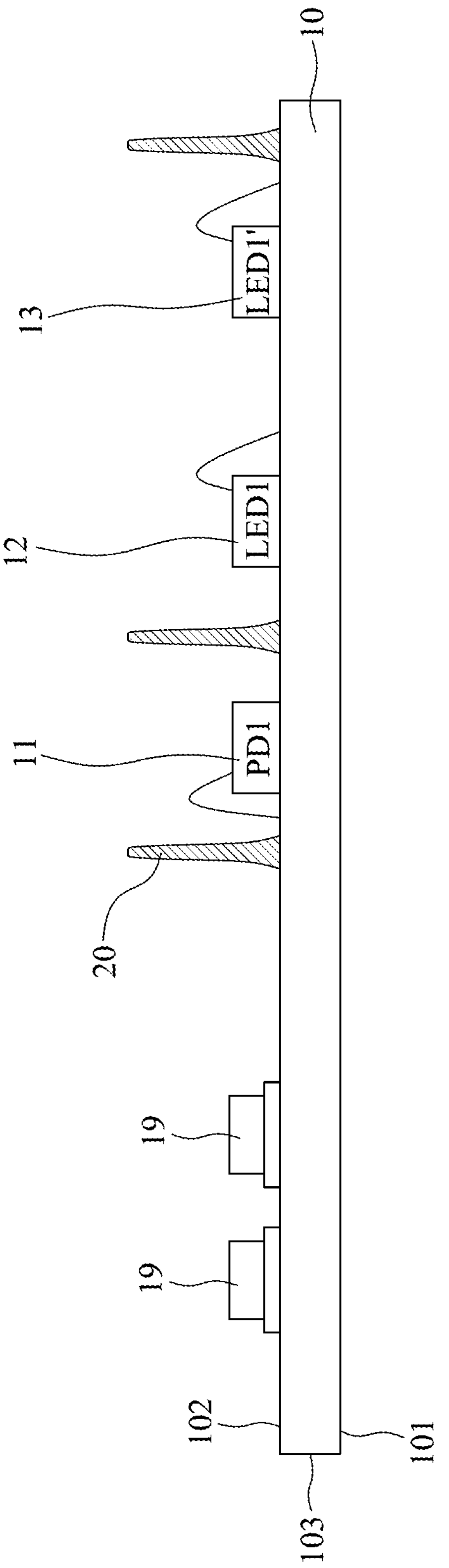
Figure 3C:
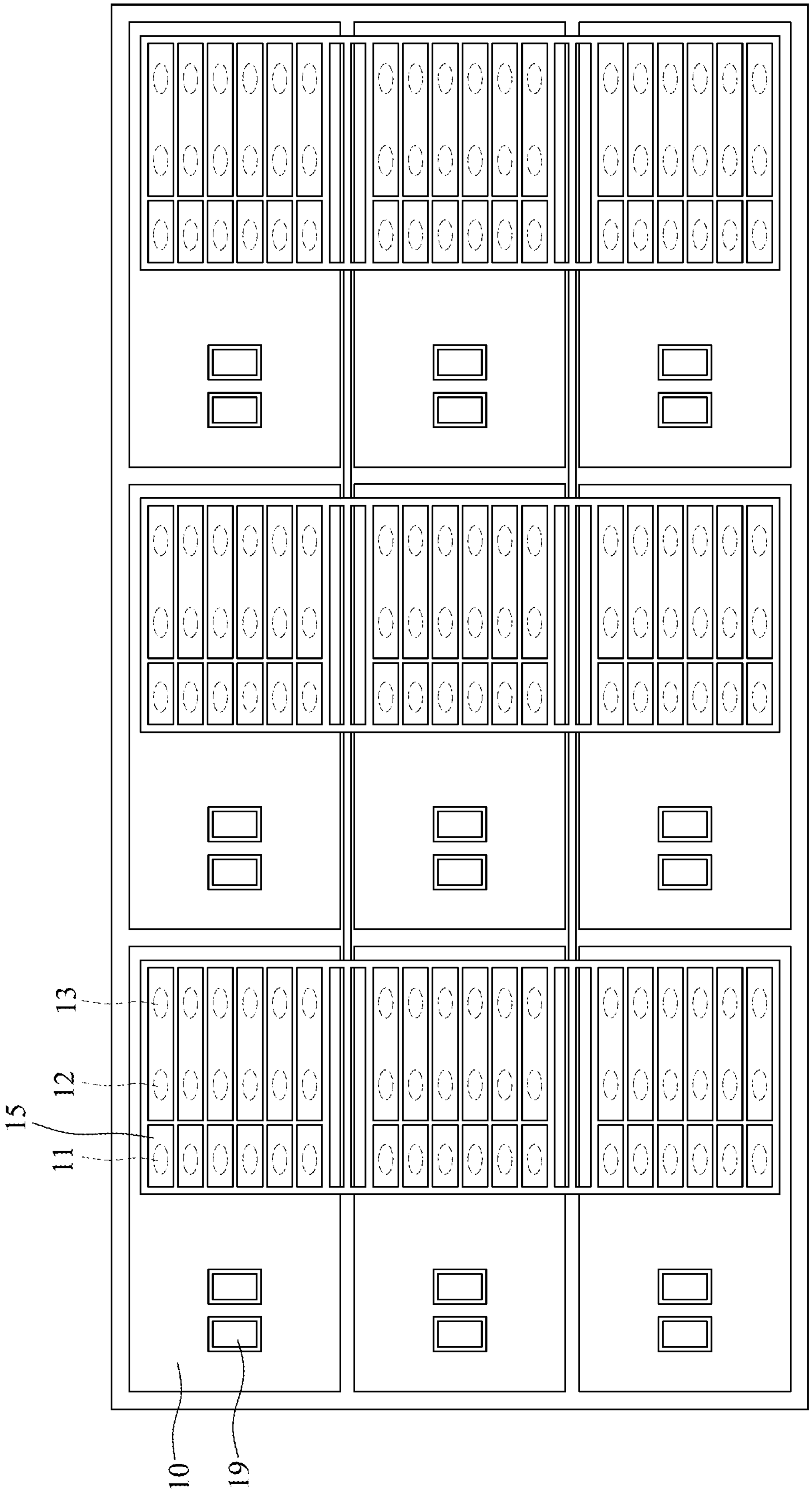

In some arrangements, from the cross-section (e.g., FIG. 2A), the light blocking structure 14 formed by a dispensing operation may include a plurality of walls and a width of one of the walls may not be constant. The dispensing operation is also illustrated in FIG. 3B-2.

Referring to FIG. 3C, the encapsulant 15 is disposed over or on the carrier 10 to cover or encapsulate the optical receivers 11, the optical emitters 12, the optical emitters 13.

In some arrangements, the encapsulant 15 may be formed by a screen printing operation and/or a dispensing operation. In some arrangements, from the cross-section (e.g., FIG. 1B), the surface 152 of the encapsulant 15 formed by a screen printing operation may be substantially planar and/or substantially parallel to the surface 102 of the carrier 10.

In some arrangements, from the cross-section (e.g., FIG. 1C), the surface 152 of the encapsulant 15 formed by a dispensing operation may be curved.

Figure 3D:
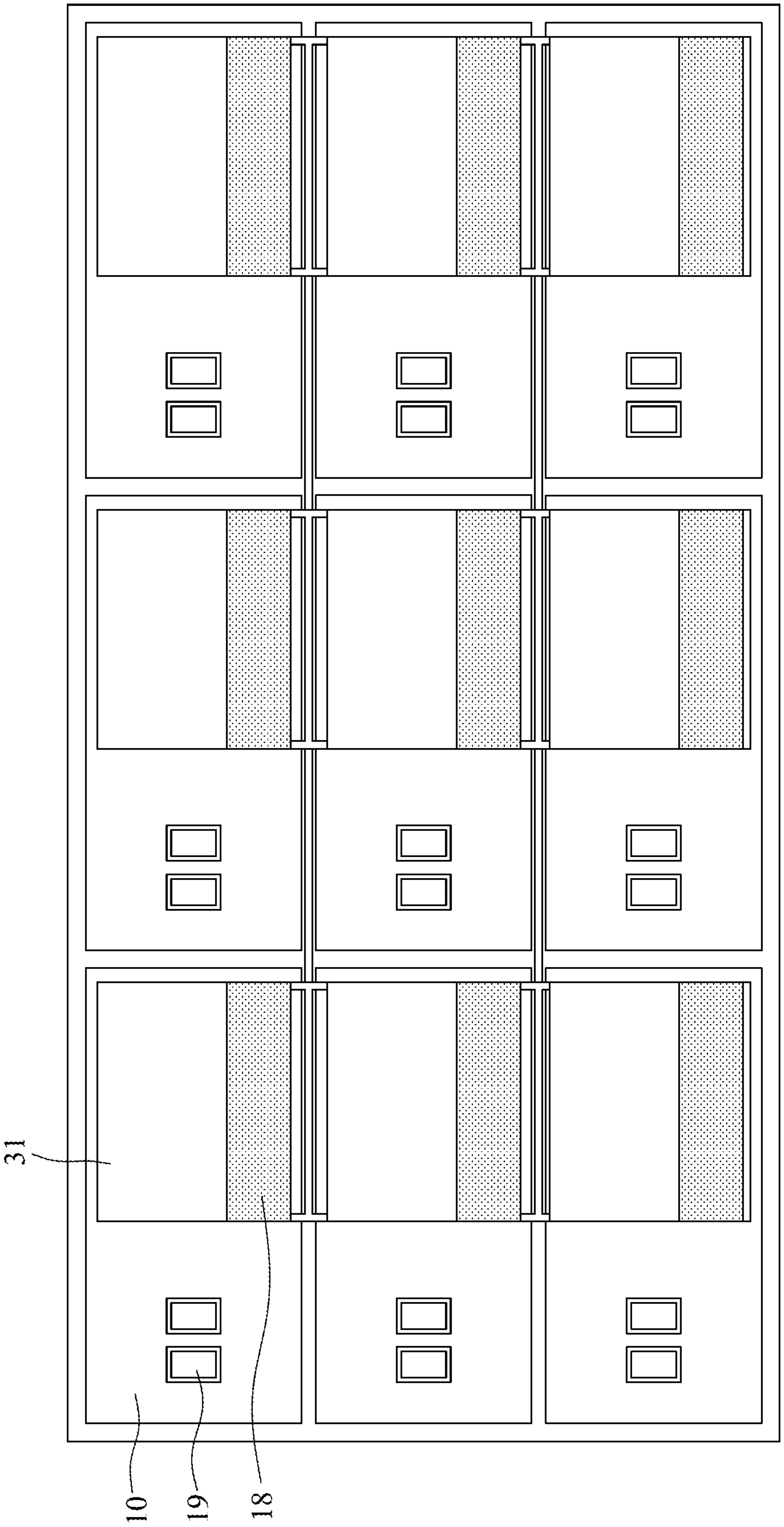

Referring to FIG. 3D, a mask 31 is disposed over or on the carrier 10 to cover the optical receivers 11, the optical emitters 12, and the optical emitters 13. Some of the optical receivers 11, the optical emitters 12, and the optical emitters 13 are exposed by the mask 31.

For example, the optical receivers PD1, PD2, PD3, PD4, the optical emitters LED1, LED2, LED3, LED4, and the optical emitters LED1', LED2', LED3', LED4' in FIG. 1A may be covered by the mask 31. The optical receivers PD5, PD6, the optical emitters LED5, LED6, and the optical emitters LED5', LED6' in FIG. 1A may be exposed by the mask 31. The optical element 18 is disposed over or on the encapsulant 15 to cover the optical receivers PD5, PD6, the optical emitters LED5, LED6, and the optical emitters LED5', LED6' in FIG. 1A.

In some arrangements, the optical element 18 may be formed by spray coating, spin coating, sputtering, evaporation, deposition, plating, other feasible operations, or a combination thereof.

Figure 3E:
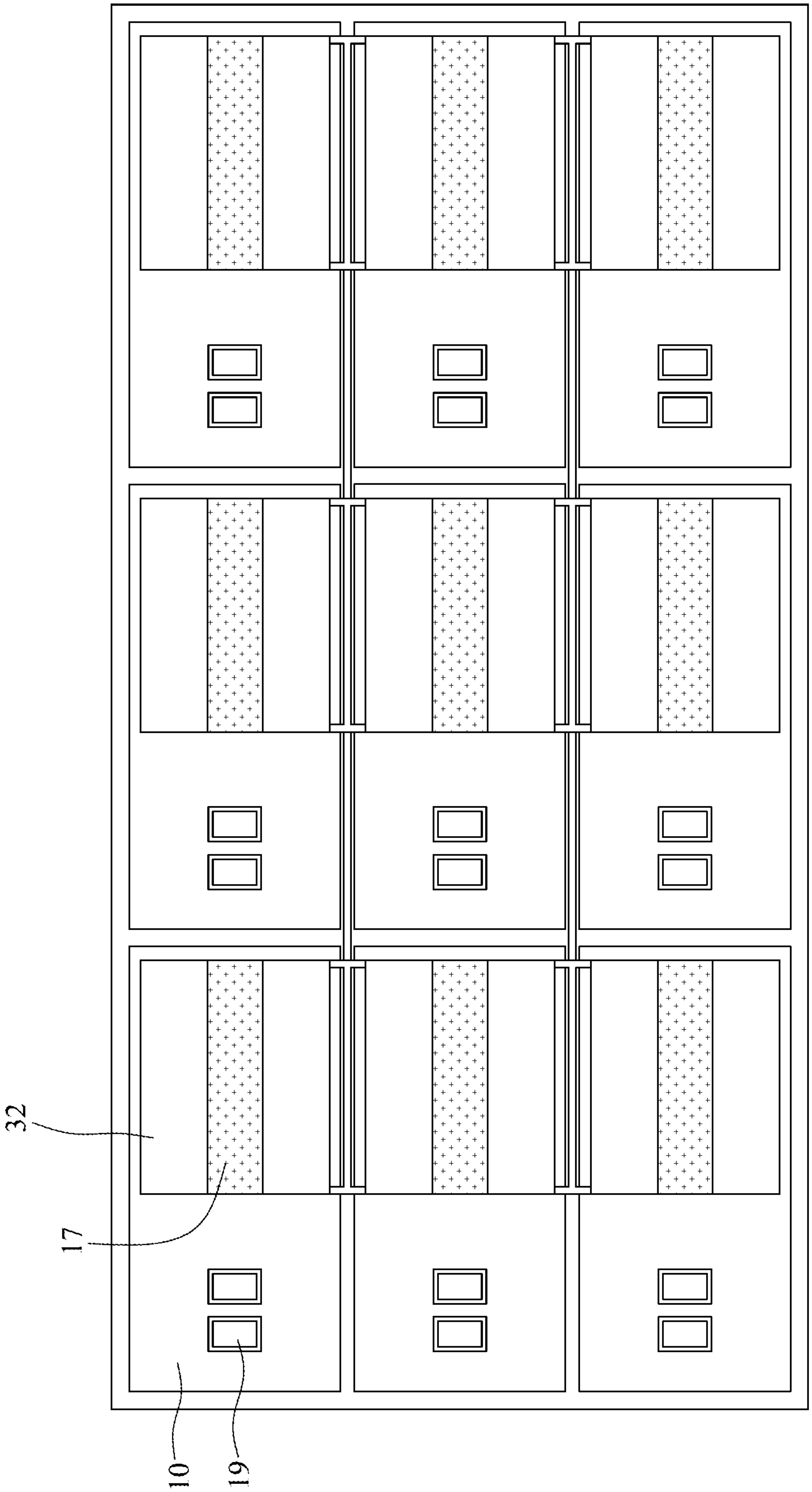

Referring to FIG. 3E, the mask 31 is removed. A mask 32 is disposed over or on the carrier 10. For example, the optical receivers PD1, PD2, the optical emitters LED1, LED2, the optical emitters LED1', LED2', the optical element 18 in FIG. 1A may be covered by the mask 32. The optical receivers PD3, PD4, the optical emitters LED3, LED4, and the optical emitters LED3', LED4' in FIG. 1A may be exposed by the mask 32. The optical element 17 is disposed over or on the encapsulant 15 to cover the optical receivers PD3, PD4, the optical emitters LED3, LED4, and the optical emitters LED3', LED4' in FIG. 1A.

Figure 3F:
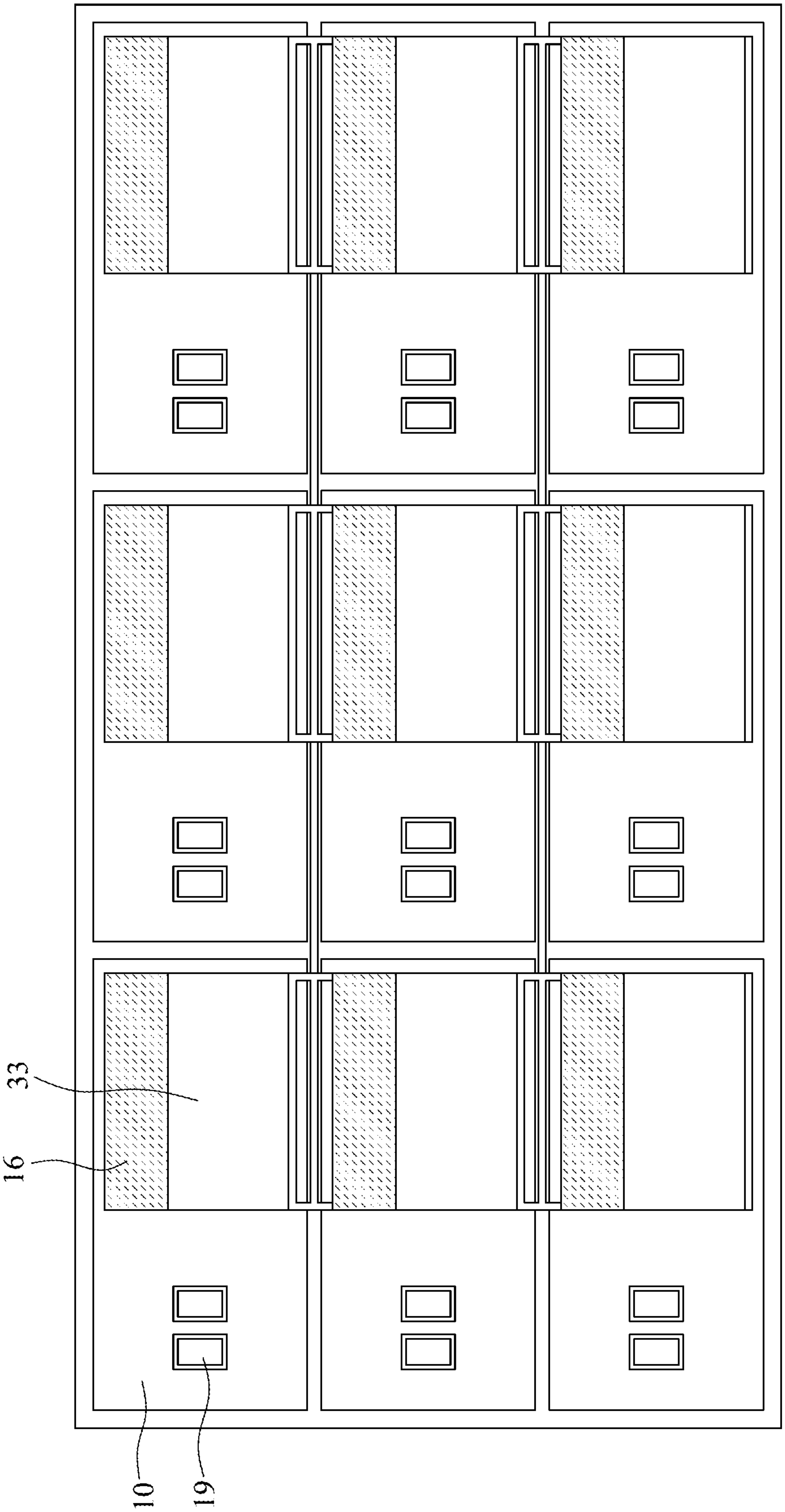

Referring to FIG. 3F, the mask 32 is removed. A mask 33 is disposed over or on the carrier 10. For example, the optical element 17, 18 in FIG. 1A may be covered by the mask 32. The optical receivers PD1, PD2, the optical emitters LED1, LED2, and the optical emitters LED1', LED2' in FIG. 1A may be exposed by the mask 32. The optical element 16 is disposed over or on the encapsulant 15 to cover the optical receivers PD1, PD2, the optical emitters LED1, LED2, and the optical emitters LED1', LED2' in FIG. 1A.

The temporary carrier 30 is singulated or diced into a plurality of individual carrier units in a singulation operation. In some arrangements, the singulation operation may be applied using a saw blade or laser cutting tool. The singulation operation may include cutting or sawing four sides of the carrier units.

Spatial descriptions, such as "above," "below," "up," "left." "right." "down," "top," "bottom," "vertical," "horizontal," "side," "higher," "lower," "upper," "over," "under," and so forth, are indicated with respect to the orientation shown in the figures unless otherwise specified. It should be understood that the spatial descriptions used herein are for purposes of illustration only, and that practical implementations of the structures described herein can be spatially arranged in any orientation or manner, provided that the merits of arrangements of this disclosure are not deviated from by such an arrangement.

As used herein, the terms "approximately," "substantially," "substantial" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, two numerical values can be deemed to be "substantially" the same or equal if a difference between the values is less than or equal to ±10% of an average of the values, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Two surfaces can be deemed to be coplanar or substantially coplanar if a displacement between the two surfaces is no greater than 5 μm, no greater than 2 μm, no greater than 1 μm, or no greater than 0.5 μm.

As used herein, the singular terms "a." "an," and "the" may include plural referents unless the context clearly dictates otherwise.

As used herein, the terms "conductive," "electrically conductive" and "electrical conductivity" refer to an ability to transport an electric current. Electrically conductive materials typically indicate those materials that exhibit little or no opposition to the flow of an electric current. One measure of electrical conductivity is Siemens per meter (S/m). Typically, an electrically conductive material is one having a conductivity greater than approximately $10^4$ S/m, such as at least $10^5$ S/m or at least $10^6$ S/m. The electrical conductivity of a material can sometimes vary with temperature. Unless otherwise specified, the electrical conductivity of a material is measured at room temperature.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified.

While the present disclosure has been described and illustrated with reference to specific arrangements thereof, these descriptions and illustrations are not limiting. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes and tolerances. There may be other arrangements of the present disclosure which are not specifically illustrated. The specification and drawings are to be regarded as illustrative rather than restrictive. Modifications may be made to adapt a particular situation, material, composition of matter, method, or process to the objective, spirit and scope of the present disclosure. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations of the present disclosure.

What is claimed is:

1. An optical module, comprising:

a carrier;

a first optical emitter disposed in a first row on the carrier and configured to emit a first light of a first wavelength band;

a first optical receiver disposed in the first row on the carrier and configured to receive the first light;

a second optical emitter disposed in a second row on the carrier and configured to emit a second light of a second wavelength band different from the first wavelength band, wherein the first optical emitter and the second optical emitter are disposed in a first column;

a second optical receiver disposed in the second row on the carrier and configured to receive the second light;

a first light blocking structure around the first optical receiver and the second optical receiver, wherein the first light blocking structure is opaque to the first wavelength band and the second wavelength band;

a second light blocking structure separating the first optical emitter from the second optical emitter and separating the first optical receiver from the second optical receiver;

an encapsulant disposed over the carrier and encapsulating the first optical receiver and the second optical receiver, wherein the encapsulant has a top surface facing away from the carrier;

a first optical filter disposed over the first optical receiver and directly contacting the top surface of the encapsulant, wherein the first optical filter is configured to allow the first light to pass through; and a second optical filter disposed over the second optical receiver and directly contacting the top surface of the encapsulant, wherein the second optical filter is configured to allow the second light to pass through, wherein a top surface and a lateral surface of the first optical filter are spaced apart from the encapsulant.

2. The optical module of claim 1, wherein the first optical filter is also disposed over the first optical emitter, and the second optical filter is also disposed over the second optical emitter.

3. The optical module of claim 2, wherein the first optical filter is spaced apart from the second optical filter by a gap, and wherein the gap is over the second light blocking structure.

4. The optical module of claim 1, wherein the first optical filter contacts a lateral surface and a top surface of the second optical filter, wherein the first optical filter is configured to filter the first light reflected from an object to be inspected, and the first optical filter is inclined with respect to the carrier, and wherein the first optical filter includes a high refractive material coating layer and a low refractive material coating layer.

5. The optical module of claim 1, wherein the first optical receiver and the second optical receiver are disposed in a second column.

6. The optical module of claim 1, wherein the top surface of the encapsulant and a top surface of the second light blocking structure define a substantially planar surface, wherein the first optical filter and the second optical filter both directly contacts the substantially planar surface, and wherein the second optical filter contacts the top surface and the lateral surface of the first optical filter.

7. The optical module of claim 1, wherein an interface between the encapsulant and the first optical filter is non-planar and recessed toward the first optical receiver, and wherein the lateral surface of the first optical filter is disposed at an elevation higher than the top surface of the encapsulant with respect to the carrier.

8. The optical module of claim 1, further comprising:

an electronic component disposed over the carrier, wherein the electronic component is configured to control the first optical emitter based on a property of the first light.

9. An optical module, comprising:

a carrier;

a light blocking structure disposed over the carrier and defining a plurality of spaces, wherein the light blocking structure has a top surface facing away from the carrier;

a plurality of optical receivers, each disposed in one of the plurality of spaces and configured to receive a reflected light from a to-be-inspected object to obtain a physiological parameter;

an encapsulant disposed in the plurality of spaces and encapsulating the plurality of optical receivers, wherein the encapsulant has a top surface facing away from the carrier; and a first optical filter directly contacting the surface of the encapsulant, wherein the top surface of the light blocking structure and the top surface of the encapsulant define a substantially planar surface, and the first optical filter directly contacting the substantially planar surface.

10. The optical module of claim 9, further comprising:

a first optical emitter disposed over the carrier and in one of the plurality of spaces, wherein the first optical emitter is configured to emit a light to the to-be-inspected object, and wherein the first optical filter is configured as a band-pass filter to the light from the first optical emitter.

11. The optical module of claim 10, wherein the top surface of the encapsulant is recessed toward the first optical emitter, and the encapsulant covers up internal surfaces of the plurality of spaces.

12. The optical module of claim 10, wherein the light blocking structure directly contacts the carrier and tapers away from the carrier.

13. The optical module of claim 10, further comprising:

a second optical filter directly contacting the substantially planar surface, wherein a passing band of the first optical filter and a passing band of the second optical filter are non-overlapping, and wherein a portion of the first optical filter and a portion of the second optical filter are overlapped with the light blocking structure.

14. An optical module, comprising:

a carrier;

a first optical receiver disposed over the carrier and configured to receive a first light of a first wavelength band;

a second optical receiver disposed over the carrier and configured to receive a second light of a second wavelength band different from the first wavelength band;

an encapsulant disposed over the carrier and encapsulating the first optical receiver and the second optical receiver, wherein the encapsulant has a top surface facing away from the carrier;

a first optical filter disposed over the first optical receiver and directly contacting the top surface of the encapsulant, wherein the first optical filter is configured to allow the first light to pass through;

a second optical filter disposed over the second optical receiver and directly contacting the top surface of the encapsulant, wherein the second optical filter is configured to allow the second light to pass through; and a light blocking structure disposed over the carrier, wherein the light blocking structure has an outermost portion surrounding the first optical receiver and the second optical receiver, and a plurality of segments extending along a first direction and a second direction, wherein one of the plurality of segments is disposed between the first optical receiver and the second optical receiver and configured to block the first light from being received by the second optical receiver, wherein the first optical filter and the second optical filter both contact a top surface of the light blocking structure facing away from the carrier, and wherein the second optical filter contacts a lateral surface and a top surface of the first optical filter.

15. The optical module of claim 14, further comprising:

a plurality of optical receivers, including the first optical receiver and the second optical receiver, disposed over the carrier, wherein the plurality of optical receivers are arranged along the first direction and separated from one another by the light blocking structure.

16. The optical module of claim 15, wherein the light blocking structure has a portion extending along the first direction till an edge of the carrier and having a surface coplanar with the edge of the carrier.

17. The optical module of claim 15, wherein a height of the one of the plurality of segments is greater than a height of the outermost portion.

18. The optical module of claim 14, further comprising:

a first optical emitter disposed over the carrier and configured to emit the first light; and a second optical emitter disposed over the carrier and configured to emit the second light, wherein the first optical filter extends over the first optical receiver, the first optical emitter, and the second optical emitter.

19. The optical module of claim 14, wherein the first optical filter extends between the top surface of the encapsulant and the top surface of the light blocking structure, and the top surface of the encapsulant is uneven.

20. The optical module of claim 19, wherein an elevation of an interface between the encapsulant and the first optical filter is lower than the top surface of the light blocking structure.

* * * * *